United States Patent
Zagar et al.

[11] Patent Number: 6,096,689
[45] Date of Patent: *Aug. 1, 2000

[54] 5-PYRAZOLYLBENZOIC ACID DERIVATIVES AS HERBICIDES

[75] Inventors: Cyrill Zagar, Ludwigshafen; Christoph-Sweder von dem Bussche-Hünnefeld, Mannheim; Elisabeth Heistracher, Ludwigshafen; Gerhard Hamprecht, Weinheim; Ralf Klintz, Gruenstadt; Peter Schäfer, Ottersheim; Karl-Otto Westphalen, Speyer; Ulf Misslitz, Neustadt; Helmut Walter, Obrigheim, all of Germany

[73] Assignee: BASF Aktiengesellschaft, Ludwigshafen, Germany

[*] Notice: This patent is subject to a terminal disclaimer.

[21] Appl. No.: 08/981,101

[22] PCT Filed: Jun. 27, 1996

[86] PCT No.: PCT/EP96/02804

§ 371 Date: Dec. 17, 1997

§ 102(e) Date: Dec. 17, 1997

[87] PCT Pub. No.: WO97/02251

PCT Pub. Date: Jan. 23, 1997

[30] Foreign Application Priority Data

Jul. 6, 1995 [DE] Germany .................... 195 24 623

[51] Int. Cl.[7] .......... A01N 43/56; C07D 231/12; C07D 231/14; C07D 231/20
[52] U.S. Cl. .......... 504/282; 504/280; 548/366.1
[58] Field of Search .......... 548/366.1; 504/280, 504/282

[56] References Cited

U.S. PATENT DOCUMENTS 5,281,571  1/1994  Woodard et al. .......... 504/225

FOREIGN PATENT DOCUMENTS

| | | |
|---|---|---|
| 2189456 | 4/1995 | Canada . |
| 361 114 | 4/1990 | European Pat. Off. . |
| 443 059 | 8/1991 | European Pat. Off. . |
| 447 055 | 9/1991 | European Pat. Off. . |
| 619 946 | 10/1994 | European Pat. Off. . |
| 647 399 | 4/1995 | European Pat. Off. . |
| 4417837 | 11/1995 | Germany . |
| 3151367 | 11/1989 | Japan . |
| 6199805 | 9/1992 | Japan . |
| 7242510 | 1/1994 | Japan . |
| 9202509 | 8/1990 | WIPO . |
| 92/06962 | 4/1992 | WIPO . |
| 94/26109 | 11/1994 | WIPO . |
| 95/30661 | 11/1995 | WIPO . |
| 95/34659 | 12/1995 | WIPO . |
| 96/15115 | 5/1996 | WIPO . |
| 97/00246 | 1/1997 | WIPO . |

*Primary Examiner*—Laura L. Stockton
*Attorney, Agent, or Firm*—Keil & Weinkauf

[57] ABSTRACT

A 5-pyrazolylbenzoic acid compound of the formula I

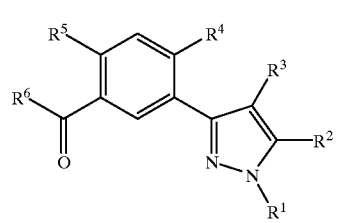

wherein $R^1$ is hydrogen, alkyl, cyanoalkyl or haloalkyl;

$R^2$ is alkoxy, alkylthio, haloalkoxy or haloalkylthio;

$R^3$ is hydrogen, cyano, nitro, halogen;

$R^4$ is halogen;

$R^5$ is cyano, halogen, alkyl, haloalkyl, alkoxy or haloalkoxy;

$R^6$ is —O—$R^7$, —S—$R^7$, —N($R^8$)—$R^7$ or —N($R^8$)—O$R^7$;

$R^7$ is —X—C($R^9$)=N—O—$R^{10}$, —X—C($R^9$)=N—O—Z—$R^{10}$, —X—O—N=C($R^{11}$,$R^{12}$), —X—SO$_2$—$R^{13}$ or an unsubstituted or substituted saturated 3- to 7-membered heterocycle or heterocyclylalkyl radical;

$R^8$ is hydrogen, alkyl, haloalkyl, alkenyl, haloalkenyl, alkynyl or alkylsulfonyl;

and $R^8$ to $R^{13}$ are as defined in the specification, or an agriculturally useful salt of a compound I, which is useful as a herbicide and for desiccating or defoliating plants.

19 Claims, No Drawings

5-PYRAZOLYLBENZOIC ACID DERIVATIVES AS HERBICIDES

This application is a 371 of PCT/EP96/02804 filed Jun. 27, 1996.

The present invention relates to novel 5-pyrazolylbenzoic acid derivatives of the formula I

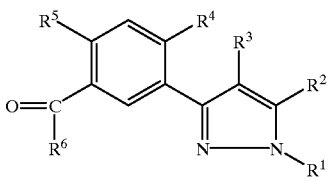

where the variables have the following meanings:

$R^1$ is hydrogen, $C_1$–$C_4$-alkyl, cyano-$C_1$–$C_4$-alkyl or $C_1$–$C_4$-haloalkyl;

$R^2$ is $C_1$–$C_4$-alkoxy, $C_1$–$C_4$-alkylthio, $C_1$–$C_4$-haloalkoxy or $C_1$–$C_4$-haloalkylthio;

$R^3$ is hydrogen, cyano, nitro, halogen;

$R^4$ is halogen;

$R^5$ is cyano, halogen, $C_1$–$C_4$-alkyl, $C_1$–$C_4$-haloalkyl, $C_1$–$C_4$-alkoxy or $C_1$–$C_4$-haloalkoxy;

$R^6$ is —O—$R^7$, —S—$R^7$, —N($R^8$)—$R^7$ or —N($R^8$)—O—$R^7$;

$R^7$ is —X—C($R^9$)=N—O—$R^{10}$, —X—C($R^9$)=N—O—Z—$R^{10}$, —X—O—N=C($R^{11}$,$R^{12}$), —X—SO$_2$—$R^{13}$ or saturated 3- to 7-membered heterocyclyl or heterocyclyl-$C_1$–$C_4$-alkyl, the heterocycle containing, besides methylene members, one to three ring members selected from the group consisting of three aza bridges and two oxygen or sulfur atoms, and it being possible, if desired, for one or two methylene groups of the heterocycle to be replaced by carbonyl, thiocarbonyl and/or sulfonyl, it being possible for the heterocycle to be unsubstituted or to have attached to it one to four substituents in each case selected from the group consisting of halogen, $C_1$–$C_4$-alkyl, $C_1$–$C_4$-alkoxy, ($C_1$–$C_4$-alkoxy)carbonyl, ($C_1$–$C_4$-alkyl)carbonyl, ($C_1$–$C_4$-alkyl)carbonyloxy and ($C_1$–$C_4$-alkyl)carbonylamino;

$R^8$ is hydrogen, $C_1$–$C_4$-alkyl, $C_1$–$C_4$-haloalkyl, $C_3$–$C_5$-alkenyl, $C_3$–$C_5$-haloalkenyl, $C_3$–$C_5$-alkynyl or $C_1$–$C_4$-alkylsulfonyl;

$R^9$ is hydrogen, cyano, $C_1$–$C_4$-alkyl, $C_1$–$C_4$-alkoxy or $C_1$–$C_4$-alkylthio;

$R^{10}$ is hydrogen, $C_1$–$C_4$-alkyl, $C_1$–$C_4$-haloalkyl, $C_1$–$C_4$-cyanoalkyl, di($C_1$–$C_4$-alkyl)amino-$C_1$–$C_4$-alkyl, $C_1$–$C_4$-alkoxy-$C_1$–$C_4$-alkyl, $C_1$–$C_4$-alkylthio-$C_1$–$C_4$-alkyl, ($C_1$–$C_4$-alkyl)carbonyl, ($C_1$–$C_4$-alkoxy)carbonyl, di($C_1$–$C_4$-alkyl)-aminocarbonyl, ($C_1$–$C_4$-haloalkyl)carbonyl, $C_3$–$C_5$-alkenyl, $C_3$–$C_5$-haloalkenyl, di($C_1$–$C_4$-alkyl)amino-$C_3$–$C_5$-alkenyl, $C_1$–$C_4$-alkoxy-$C_3$–$C_5$-alkenyl, $C_1$–$C_4$-alkylthio-$C_3$–$C_5$-alkenyl, $C_3$–$C_5$-alkynyl, $C_3$–$C_5$-haloalkynyl, $C_3$–$C_7$-cycloalkyl which, if desired, can have attached to it one to three $C_1$–$C_3$-alkyl radicals, or is phenyl, benzoyl or 5- or 6-membered heteroaryl which contains one to three hetero atoms selected from the group consisting of three nitrogen atoms and one oxygen or sulfur atom, it being possible for the phenyl and heteroaryl rings to be unsubstituted or to have attached to each substitutable ring member one of the following substituents: nitro, cyano, halogen, $C_1$–$C_4$-alkyl, $C_1$–$C_4$-haloalkyl or $C_1$–$C_4$-alkoxy;

$R^{11}$, $R^{12}$ independently of one another are hydrogen, $C_1$–$C_4$-alkyl, $C_1$–$C_4$-haloalkyl, $C_1$–$C_4$-alkoxy-$C_1$–$C_4$-alkyl, $C_3$–$C_5$-alkenyl, $C_3$–$C_5$-haloalkenyl, $C_3$–$C_5$-alkynyl, $C_3$–$C_5$-haloalkynyl, $C_3$–$C_7$-cycloalkyl, which, if desired, can have attached to it one to three $C_1$–$C_3$-alkyl radicals, or are phenyl which, if desired, can have attached to each substitutable ring member one of the following substituents: nitro, cyano, halogen, $C_1$–$C_4$-alkyl, $C_1$–$C_4$-haloalkyl or $C_1$–$C_4$-alkoxy, or $R^{11}$ and $R^{12}$ together with the joint carbon atom to which they are bonded form a saturated 3- to 8-membered ring which, if desired, can contain, besides methylene members, one or two oxygen, sulfur and/or aza ring members, it being possible for the ring to be unsubstituted or to have attached to it one to four $C_1$–$C_4$-alkyl radicals;

$R^{13}$ is $C_1$–$C_4$-alkyl, $C_1$–$C_4$-haloalkyl, $C_1$–$C_4$-cyanoalkyl, di($C_1$–$C_4$-alkyl)amino-($C_1$–$C_4$-alkyl), $C_1$–$C_4$-alkoxy-$C_1$–$C_4$-alkyl, $C_1$–$C_4$-alkylthio-$C_1$–$C_4$-alkyl, $C_3$–$C_5$-alkenyl, $C_3$–$C_5$-haloalkenyl, di($C_1$–$C_4$-alkyl)amino-$C_3$–$C_5$-alkenyl, $C_1$–$C_4$-alkoxy-$C_3$–$C_5$-alkenyl, $C_1$–$C_4$-alkylthio-$C_3$–$C_5$-alkenyl, $C_3$–$C_5$-alkynyl, $C_3$–$C_5$-haloalkynyl, $C_3$–$C_7$-cycloalkyl which, if desired, can have attached to it one to three $C_1$–$C_3$-alkyl radicals, or is phenyl, or is 5- or 6-membered heteroaryl which contains one to three hetero atoms selected from the group consisting of three nitrogen atoms and one oxygen or sulfur atom, it being possible for the phenyl and heteroaryl ring to be unsubstituted or to have attached to each substitutable ring member one of the following substituents: nitro, cyano, halogen, $C_1$–$C_4$-alkyl, $C_1$–$C_4$-haloalkyl or $C_1$–$C_4$-alkoxy;

X and Z independently of one another are $C_1$–$C_4$-alkylene chains which can be unsubstituted or can have attached to them one to four substituents in each case selected from the group consisting of halogen, $C_1$–$C_4$-alkyl, $C_1$–$C_4$-haloalkyl and $C_1$–$C_4$-alkoxy; and to the agriculturally useful salts of the compounds I.

Furthermore, the invention relates to the use of these compounds as herbicides, to herbicidal compositions which comprise the compounds I as active ingredients, to processes for the preparation of these herbicidal compositions, and to methods of controlling undesirable vegetation using the compounds I.

WO 92/06 962, EP-A 361 114 and EP-A 443 059 already disclose 3-phenylpyrazoles of the type of the compounds I having an ester, thioester or acid amide group on the phenyl ring in the metaposition relative to the pyrazole radical.

Moreover, JP-A 03/151 367 discloses that compounds of the formula II

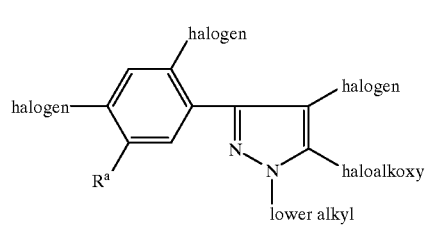

where $R^a$ is, inter alia, —C($R^b$)$_2$COR$^c$, —CH=CH—COR$^d$ or —C(COR$^e$)=CHR$^f$ and $R^b$ is hydrogen or lower alkyl, $R^c$ is hydroxyl, lower alkoxy or lower alkylthio, $R^d$ is lower alkyl, lower alkoxy or lower alkenyloxy, $R^e$ is lower alkoxy or lower alkenyloxy and $R^f$ is hydroxyl or lower alkoxy, are also herbicidally active.

Moreover, JP 06/199 805 also discloses that compounds of the formula IIIa

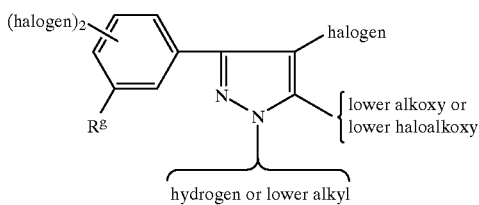

where $R^g$ is, inter alia, carboxyl, lower alkoxycarbonyl or lower alkylthiocarbonylalkoxycarbonyl, and EP-A 447 055 discloses that compounds of the formula IIIb

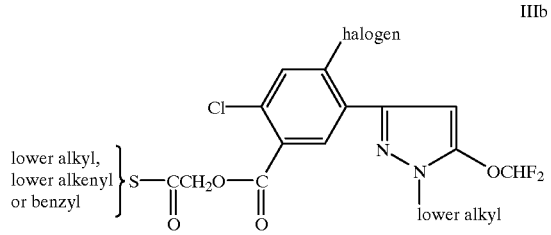

are suitable as herbicides.

EP-A 619 946 describes synergistic herbicidal compositions which comprise 3-phenylpyrazole derivatives of the formula IIIc

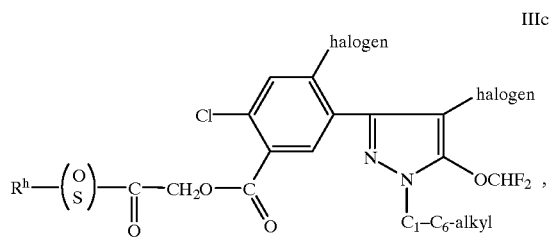

where $R^h$ is hydrogen, $C_1$–$C_6$-alkyl, $C_3$–$C_6$-cycloalkyl, $C_1$–$C_6$-haloalkyl, $C_2$–$C_6$-alkenyl or $C_2$–$C_6$-alkynyl.

EP-A 647 399 describes a pesticidally active, aqueous suspension of certain 3-phenylpyrazoles, inter alia compounds of the formula IIId

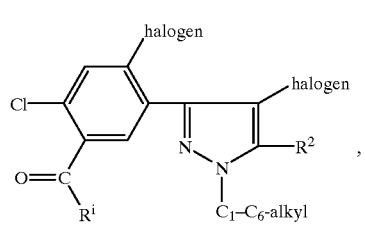

where $R^i$ is $C_1$–$C_6$-alkyl, $C_1$–$C_6$-haloalkyl, $C_2$–$C_6$-alkenyl, $C_2$–$C_6$-alkynyl or —CH(H/$C_1$–$C_6$-alkyl)—CO—(O/S)—$R^k$ where $R^k$=hydrogen, $C_1$–$C_6$-alkyl, $C_1$–$C_6$-haloalkyl, $C_2$–$C_6$-alkenyl or $C_2$–$C_6$-alkynyl.

Furthermore, WO 92/02509 describes certain phenylpyrazoles as herbicidally active ingredients which can have attached to them on the phenyl ring an ester, thioester or acid amide group, inter alia, and on the pyrazole ring a $C_1$–$C_5$-alkylsulfonyl or halogen-substituted $C_1$–$C_5$-alkylsulfonyl group, inter alia. A suitable choice of the substituents allows precursors of these compounds to be constructed with alkylthio or haloalkylthio on the pyrazole ring and which belong to the same type as the present compounds I.

Finally, WO 95/30661 discloses phenylthiocarboxamides which can have attached to them on the phenyl ring in the ortho-position relative to the thiocarboxamide group an ester, thioester or acid-amide group, inter alia, and in the para-position a pyrazol-3-yl ring, inter alia, for use as herbicides. A suitable choice of the substituents would give the corresponding cyanophenyl precursors of these compounds which are of the same type as the 5-pyrazolylbenzoic acid derivatives I where $R^5$=cyano.

However, the herbicidal properties of the known herbicides are not always entirely satisfactory relative to the weeds. It was therefore an object of the present invention to provide novel, in particular herbicidally active, compounds with which a targeted control of undesirable plants can be effected better than this was possible to date.

Another object was to provide novel compounds which act as desiccants/defoliants.

Accordingly, we have found that this object is achieved by the present 5-pyrazolylbenzoic acid derivatives of the formula I and their herbicidal action.

There have also been found herbicidal compositions which comprise the compounds I and which have a very good herbicidal action. Moreover, there were found processes for the preparation of these compositions and methods of controlling undesirable vegetation using the compounds I.

Furthermore, it has been found that the compounds I are also suitable for defoliating and desiccating parts of plants, suitable plants being crop plants such as cotton, potato, oil seed rape, sunflower, soya bean or field beans, in particular cotton. Relating to this, there have been found compositions for desiccating and/or defoliating plants, processes for the preparation of these compositions and methods for desiccating and/or defoliating plants using the compounds I.

Depending on the substitution pattern, the compounds of the formula I can contain one or more chiral centers, in which case they are present in the form of enantiomer or diastereomer mixtures. The invention relates to the pure enantiomers or diastereomers and also to their mixtures.

Suitable agriculturally useful salts are, especially, the salts of those cations or the acid addition salts of those acids whose cations, or anions, respectively, do not adversely affect the herbicidal action of the compounds I. Thus, particularly suitable cations are the ions of the alkali metals, preferably sodium and potassium, of the alkaline earth metals, preferably calcium, magnesium and barium, and of the transition metals, preferably manganese, copper, zinc and iron, and the ammonium ion which, if desired, can have attached to it one to four $C_1$–$C_4$-alkyl substituents and/or one phenyl or benzyl substituent, preferably diisopropylammonium, tetramethylammonium, tetrabutylammonium, trimethylbenzylammonium, moreover phosphonium ions, sulfonium ions, preferably tri($C_1$–$C_4$-alkyl)sulfonium, and sulfoxonium ions, preferably tri($C_1$–$C_4$-alkyl)sulfoxonium.

Anions of useful acid addition salts are mainly chloride, bromide, fluoride, hydrogen sulfate, sulfate, dihydrogenphosphate, hydrogenphosphate, phosphate, nitrate, hydrogencarbonate, carbonate, hexafluorosilicate, hexafluorophosphate, benzoate, and the anions of $C_1$–$C_4$-alkanoic acids, preferably formate, acetate, propionate and butyrate.

The organic moieties mentioned for the substituents $R^1$ to $R^3$, $R^5$ and $R^7$ to $R^{13}$ or as radicals on alkylene chains, phenyl rings or heterocycles represent collective terms for individual enumerations of the individual group members. All carbon chains, ie. all alkyl, cyanoalkyl, haloalkyl, alkoxy, alkylthio, haloalkoxy, haloalkylthio, alkylcarbonyl, haloalkylcarbonyl, alkoxycarbonyl, alkylcarbonyloxy, alkylcarbonylamino, alkenyl, haloalkenyl, alkynyl, haloalkynyl and alkylsulfonyl moieties can be straight-chain or branched. Unless otherwise specified, halogenated substituents have attached to them preferably one to five identical or different halogen atoms. Halogen in each case represents fluorine, chlorine, bromine or iodine, in particular fluorine or chlorine.

Further examples of meanings are:

$C_1$–$C_3$-alkyl: methyl, ethyl, n-propyl or 1-methylethyl, in particular methyl;

$C_1$–$C_4$-alkyl and the alkyl moieties of ($C_1$–$C_4$-alkyl)carbonyl, ($C_1$–$C_4$-alkyl)carbonyloxy, ($C_1$–$C_4$-alkyl)carbonylamino, $C_1$–$C_4$-alkoxy-$C_1$–$C_4$-alkyl, $C_1$–$C_4$-alkylthio-$C_1$–$C_4$-alkyl, di($C_1$–$C_4$-alkyl)aminocarbonyl, di($C_1$–$C_4$-alkyl)amino-$C_1$–$C_4$-alkyl and di($C_1$–$C_4$-alkyl)amino-$C_3$–$C_5$-alkenyl: methyl, ethyl, n-propyl, 1-methylethyl, n-butyl, 1-methylpropyl, 2-methylpropyl or 1,1-dimethylethyl, in particular methyl or ethyl;

$C_1$–$C_4$-alkylene: methylene, ethane-1,2-diyl, propane-1,2-diyl, propane-1,3-diyl, butane-1,2-diyl, butane-1,3-diyl, butane-1,4-diyl or butane-2,3-diyl;

$C_1$–$C_4$-haloalkyl and the haloalkyl moiety of ($C_1$–$C_4$-haloalkyl)carbonyl: a $C_1$–$C_4$-alkyl radical as mentioned above which is partially or fully substituted by fluorine, chlorine, bromine and/or iodine, e.g. chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl,3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl, in particular trifluoromethyl or 1,2-dichloroethyl;

cyano-$C_1$–$C_4$-alkyl: cyanomethyl, 1-cyanoethyl, 2-cyanoethyl, 1-cyanoprop-1-yl, 2-cyanoprop-1-yl, 3-cyanoprop-1-yl, 1-cyanobut-1-yl, 2-cyanobut-1-yl, 3-cyanobut-1-yl, 4-cyanobut-1-yl, 1-cyanobut-2-yl, 2-cyanobut-2-yl, 3-cyanobut-2-yl, 3-cyanobut-2-yl, 4-cyanobut-2-yl, 1-(cyanomethyl)eth-1-yl, 1-(cyanomethyl) 1-(methyl)eth-1-yl or 1-(cyanomethyl)-prop-1-yl, preferably cyanomethyl or 2-cyanoethyl;

heterocyclyl-$C_1$–$C_4$-alkyl: heterocyclylmethyl, 1-(heterocyclyl)ethyl, 2-(heterocyclyl)ethyl, 1-(heterocyclyl)-prop-1-yl, 2-(heterocyclyl)prop-1-yl, 3-(heterocyclyl)-prop-1-yl, 1-(heterocyclyl)but-1-yl, 2-(heterocyclyl)-but-1-yl, 3-(heterocyclyl)but-1-yl, 4-(heterocyclyl)but-1-yl, 1-(heterocyclyl)but-2-yl, 2-(heterocyclyl)but-2-yl, 3-(heterocyclyl)but-2-yl, 3-(heterocyclyl)but-2-yl, 4-(heterocyclyl)but-2-yl, 1-(heterocyclylmethyl)eth-1-yl, 1-(heterocyclylmethyl)-1-(methyl)eth-1-yl or 1-(heterocyclylmethyl)prop-1-yl, preferably (heterocyclyl)methyl or 2-(heterocyclyl)ethyl;

$C_1$–$C_4$-alkylsulfonyl: methylsulfonyl, ethylsulfonyl, n-propylsulfonyl, 1-methylethylsulfonyl, n-butylsulfonyl, 1-methylpropylsulfonyl, 2-methylpropylsulfonyl, 1,1-dimethylethylsulfonyl, n-pentylsulfonyl, 1-methylbutylsulfonyl, 2-methylbutylsulfonyl, 3-methylbutylsulfonyl, 2,2-dimethylpropylsulfonyl, 1-ethylpropylsulfonyl, 1,1-dimethylpropylsulfonyl, 1,2-dimethylpropylsulfonyl, n-hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl, in particular methylsulfonyl or ethylsulfonyl;

$C_1$–$C_4$-alkoxy and the alkoxy moieties of ($C_1$–$C_4$-alkoxy)carbonyl, $C_1$–$C_4$-alkoxy-$C_1$–$C_4$-alkyl and $C_1$–$C_4$-alkoxy-$C_3$–$C_5$-alkenyl: methoxy, ethoxy, n-propoxy, 1-methylethoxy, n-butoxy, 1-methylpropoxy, 2-methylpropoxy or 1,1-dimethylethoxy, in particular methoxy, ethoxy, 1-methylethoxy or 1,1-dimethylethoxy;

$C_1$–$C_4$-alkylthio and the alkylthio moieties of $C_1$–$C_4$-alkylthio-$C_1$–$C_4$-alkyl and $C_1$–$C_4$-alkylthio-$C_3$–$C_5$-alkenyl: methylthio, ethylthio, n-propylthio, 1-methylethylthio, n-butylthio, 1-methylpropylthio, 2-methylpropylthio or 1,1-dimethylethylthio, in particular methylthio or ethylthio;

$C_1$–$C_4$-haloalkoxy: $C_1$–$C_4$-alkoxy as mentioned above which is partially or fully substituted by fluorine, chlorine and/or bromine, e.g. chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, bromodifluoromethoxy, 1-fluoroethoxy, 2-fluoroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy or nonafluorobutoxy, preferably difluoromethoxy, trifluoromethoxy or pentafluoroethoxy;

$C_1$–$C_4$-haloalkylthio: $C_1$–$C_4$-alkylthio as mentioned above which is partially or fully substituted by fluorine, chlorine and/or bromine, e.g. difluoromethylthio, trifluoromethylthio, chlorodifluoromethylthio, bromodifluoromethylthio, 2-fluoroethylthio, 2-chloroethylthio, 2-bromoethylthio, 2-iodoethylthio, 2,2-difluoroethylthio, 2,2,2-trifluoroethylthio, 2,2,2-trichloroethylthio, 2-chloro-2-fluoroethylthio, 2-chloro-2,2-difluoroethylthio, 2,2-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio or 4-bromobutylthio;

$C_3$–$C_6$-alkenyl and the alkenyl moieties of $C_1$–$C_4$-alkoxy-$C_3$–$C_6$-alkenyl, $C_1$–$C_4$-alkylthio-$C_3$–$C_6$-alkenyl and di($C_1$–$C_4$-alkyl)amino-$C_3$–$C_6$-alkenyl: prop-1-en-1-yl, prop-2-en-1-yl, 1-methylethenyl, n-buten-1-yl, n-buten-2-yl, n-buten-3-yl, 1-methylprop-1-en-1-yl, 2-methylprop-1-en-1-yl, 1-methylprop-2-en-1-yl or 2-methylprop-2-en-1-yl, n-penten-1-yl, n-penten-2-yl, n-penten-3-yl, n-penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, n-hex-1-en-1-yl, n-hex-2-en-1-yl, n-hex-3-en-1-yl, n-hex-4-en-1-yl, n-hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methyl-pent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl or 1-ethyl-2-methylprop-2-en-1-yl;

$C_3$–$C_6$-alkynyl: prop-1-yn-1-yl, prop-2-yn-1-yl, but-1-yn-1-yl, but-1-yn-3-yl, but-1-yn-4-yl, but-2-yn-1-yl, pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl;

$C_3$–$C_6$-haloalkenyl: $C_3$–$C_6$-alkenyl as mentioned above which is partially or fully substituted by fluorine, chlorine and/or bromine, e.g. 2-chloroallyl, 3-chloroallyl, 3,3-dichloroallyl or pentafluoroallyl, in particular $C_3$- or $C_4$-haloalkenyl;

$C_3$–$C_6$-haloalkynyl: $C_3$–$C_6$-alkynyl as mentioned above which is partially or fully substituted by fluorine, chlorine and/or bromine, e.g. 4-chlorobut-2-yn-1-yl;

$C_3$–$C_7$-cycloalkyl: cyclopropyl, cyclobutyl, cyclopentyl, cyclohexyl or cycloheptyl, in particular $C_3$–$C_6$-cycloalkyl;

saturated 3- to 7-membered heterocyclyl and the heterocyclyl moiety of heterocyclyl-$C_1$–$C_4$-alkyl: e.g. oxiranyl, thiiranyl, aziridin-1-yl, aziridin-2-yl, diaziridin-1-yl, diaziridin-3-yl, oxetan-2-yl, oxetan-3-yl, thietan-2-yl, thietan-3-yl, azetidin-1-yl, azetidin-2-yl, azetidin-3-yl, tetrahydrofuran-2-yl, tetrahydrofuran-3-yl, tetrahydrothiophen-2-yl, tetrahydrothiophen-3-yl, pyrrolidin-1-yl, pyrrolidin-2-yl, pyrrolidin-3-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-oxazolidin-2-yl, 1,3-oxazolidin-3-yl, 1,3-oxazolidin-4-yl, 1,3-oxazolidin-5-yl, 1,2-oxazolidin-2-yl, 1,2-oxazolidin-3-yl, 1,2-oxazolidin-4-yl, 1,2-oxazolidin-5-yl, 1,3-dithiolan-2-yl, 1,3-dithiolan-4-yl, pyrrolidin-1-yl, pyrrolidin-2-yl, pyrrolidin-5-yl, tetrahydropyrazol-1-yl, tetrahydropyrazol-3-yl, tetrahydropyrazol-4-yl, tetrahydropyran-2-yl, tetrahydropyran-3-yl, tetrahydropyran-4-yl, tetrahydrothiopyran-2-yl, tetrahydrothiopyran-3-yl, tetrahydropyran-4-yl, piperidin-1-yl, piperidin-2-yl, piperidin-3-yl, piperidin-4-yl, 1,3-dioxan-2-yl, 1,3-dioxan-4-yl, 1,3-dioxan-5-yl, 1,4-dioxan-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, morpholin-2-yl, morpholin-3-yl, morpholin-4-yl, hexahydropyridazin-1-yl, hexahydropyridazin-3-yl, hexahydropyridazin-4-yl, hexahydropyrimidin-1-yl, hexahydropyrimidin-2-yl, hexahydropyrimidin-4-yl, hexahydropyrimidin-5-yl, piperazin-1-yl, piperazin-2-yl, piperazin-3-yl, hexahydro-1,3,5-triazin-1-yl, hexahydro-1,3,5-triazin-2-yl, oxepan-2-yl, oxepan-3-yl, oxepan-4-yl, thiepan-2-yl, thiepan-3-yl, thiepan-4-yl, 1,3-dioxepan-2-yl, 1,3-dioxepan-4-yl, 1,3-dioxepan-5-yl, 1,3-dioxepan-6-yl, 1,3-dithiepan-2-yl, 1,3-dithiepan-2-yl, 1,3-dithiepan-2-yl, 1,3-dithiepan-2-yl, 1,4-dioxepan-2-yl, 1,4-dioxepan-7-yl, hexahydroazepin-1-yl, hexahydroazepin-2-yl, hexahydroazepin-3-yl, hexahydroazepin-4-yl, hexahydro-1,3-diazepin-1-yl, hexahydro-1,3-diazepin-2-yl, hexahydro-1,3-diazepin-4-yl, hexahydro-1,4-diazepin-1-yl or hexahydro-1,4-diazepin-2-yl;

5- or 6-membered heteroaryl: in particular furyl, such as 2-furyl and 3-furyl, thienyl, such as 2-thienyl and 3-thienyl, pyrrolyl, such as 2-pyrrolyl and 3-pyrrolyl, isoxazolyl, such as 3-isoxazolyl, 4-isoxazolyl and 5-isoxazolyl, isothiazolyl, such as 3-isothiazolyl, 4-isothiazolyl and 5-isothiazolyl, pyrazolyl, such as 3-pyrazolyl, 4-pyrazolyl and 5-pyrazolyl, oxazolyl, such as 2-oxazolyl, 4-oxazolyl and 5-oxazolyl, thiazolyl, such as 2-thiazolyl, 4-thiazolyl and 5-thiazolyl, imidazolyl, such as 2-imidazolyl and 4-imidazolyl, oxadiazolyl, such as 1,2,4-oxadiazol-3-yl, 1,2,4-oxadiazol-5-yl and 1,3,4-oxadiazol-2-yl, thiadiazolyl, such as 1,2,4-thiadiazol-3-yl, 1,2,4-thiadiazol-5-yl and 1,3,4-thiadiazol-2-yl, triazolyl, such as 1,2,4-triazol-1-yl, 1,2,4-triazol-3-yl and 1,2,4-triazol-4-yl, pyridinyl, such as 2-pyridinyl, 3-pyridinyl and 4-Pyridinyl, pyridazinyl, such as 3-pyridazinyl and 4-pyridazinyl, pyrimidinyl, such as 2-pyrimidinyl, 4-pyrimidinyl and 5-pyrimidinyl, furthermore 2-pyrazinyl, 1,3,5-triazin-2-yl and 1,2,4-triazin-3-yl, in particular pyridyl, pyrimidyl, furanyl and thienyl.

All phenyl rings and heterocyclic rings are preferably unsubstituted or have attached to them a halogen, methyl, trifluoromethyl or methoxy substituent.

With a view to the use of the 5-pyrazolylbenzoic acid derivatives I as herbicides, preferred compounds I are those where the substituents have the following meanings, in each case alone or in combination:

$R^1$ is hydrogen or $C_1$–$C_4$-alkyl, in particular $C_1$–$C_4$-alkyl; methyl is particularly preferred;

$R^2$ is $C_1$–$C_4$-haloalkoxy, in particular difluoromethoxy;

$R^3$ is hydrogen or halogen, in particular halogen; chlorine is particularly preferred;

$R^4$ is fluorine or chlorine;

$R^5$ is halogen or $C_1$–$C_4$-haloalkyl, in particular halogen; chlorine is particularly preferred;

$R^6$ is —O—$R^7$ or —N($R^8$)—$R^7$;

$R^7$ is —X—C($R^9$)=N—O—Z—$R^{10}$, —X—O—N=C($R^{11}$,$R^{12}$), —X—SO$_2$—$R^{13}$ or saturated 3- to 6-membered heterocyclyl or heterocyclyl-$C_1$–$C_4$-alkyl, the heterocycle containing, besides methylene members, one to three ring members selected from the group consisting of three aza bridges and two oxygen or sulfur atoms, and it being possible, if desired, for one or two methylene groups of the heterocycle to be replaced by carbonyl, thiocarbonyl and/or sulfonyl, it being possible for the heterocycle to be unsubstituted or to have attached to it one to four substituents in each case selected from the group consisting of halogen, $C_1$–$C_4$-alkyl, $C_1$–$C_4$-alkoxy, ($C_1$–$C_4$-alkoxy)carbonyl, ($C_1$–$C_4$-alkyl)carbonyl, ($C_1$–$C_4$-alkyl)carbonyloxy and ($C_1$–$C_4$-alkyl)carbonylamino; in particular —X—C($R^9$)=N—O—Z—$R^{10}$ or —X—O—N=C($R^{11}$, $R^{12}$);

$R^8$ is hydrogen or $C_1$–$C_4$-alkyl, in particular hydrogen or methyl;

$R^9$ is hydrogen or $C_1$–$C_4$-alkyl, in particular hydrogen or methyl;

$R^{10}$ is hydrogen, $C_1$–$C_4$-alkyl, $C_1$–$C_4$-haloalkyl, $C_1$–$C_4$-alkoxy-$C_1$–$C_4$-alkyl, $C_3$–$C_5$-alkenyl, $C_3$–$C_5$-haloalkenyl, $C_3$–$C_5$-alkynyl, $C_3$–$C_5$-haloalkynyl, $C_3$–$C_7$-cycloalkyl, which, if desired, can have attached to it one to three $C_1$–$C_3$-alkyl radicals, or is phenyl, benzoyl or 5- or 6-membered heteroaryl which contains one to three hetero atoms selected from the group consisting of three nitrogen atoms and one oxygen or sulfur atom, it being possible for the phenyl and heteroaryl rings to be unsubstituted or to have attached to each substitutable ring member one of the following substituents: nitro, cyano, halogen, $C_1$–$C_4$-alkyl, $C_1$–$C_4$-haloalkyl or $C_1$–$C_4$-alkoxy; in particular hydrogen, $C_1$–$C_4$-alkyl, $C_1$–$C_4$-haloalkyl, $C_3$–$C_5$-alkenyl, $C_3$–$C_5$-alkynyl, phenyl, benzoyl or 5- or 6-membered heteroaryl which contains one to three hetero atoms selected from the group consisting of three nitrogen atoms and one oxygen or sulfur atom, it being possible for the phenyl and heteroaryl rings to be unsubstituted or to have attached to each substitutable ring member one of the following substituents: nitro, cyano, halogen or $C_1$–$C_4$-alkyl;

$R^{11}$, $R^{12}$ independently of one another are hydrogen, $C_1$–$C_4$-alkyl, $C_1$–$C_4$-haloalkyl, $C_3$–$C_5$-alkenyl, $C_3$–$C_5$-alkynyl, $C_3$–$C_7$-cycloalkyl or phenyl which, if desired, can have attached to each substitutable ring member one of the following substituents: nitro, cyano, halogen and $C_1$–$C_4$-alkyl, in particular $C_1$–$C_4$-alkyl, or $R^{11}$ and $R^{12}$ together with the joint carbon atom to which they are bonded form a saturated 5- or 6-membered carbocyclic ring;

$R^{13}$ is $C_1$–$C_4$-alkyl, $C_1$–$C_4$-haloalkyl, $C_1$–$C_4$-alkoxy-$C_1$–$C_4$-alkyl, $C_3$–$C_5$-alkenyl, $C_3$–$C_5$-haloalkenyl, $C_3$–$C_5$-alkynyl, phenyl or 5- or 6-membered heteroaryl which contains one to three hetero atoms selected from the group consisting of three nitrogen atoms and one oxygen or sulfur atom, it being possible for the phenyl and heteroaryl ring to be unsubstituted or to have attached to each substitutable ring member a halogen or $C_1$–$C_4$-alkyl substituent, in particular $C_1$–$C_4$-alkyl or phenyl;

X and Z independently of one another are $C_1$–$C_4$-alkylene chains which can be unsubstituted or have attached to them one to four halogen and/or $C_1$–$C_4$-alkyl substituents, in particular methylene, ethane-1,2-diyl or propane-1,3-diyl.

Very particularly preferred are the compounds Ia listed in Table 1 below (=I where $R^1$=methyl; $R^2$=difluoromethoxy; $R^3$, $R^4$ nd $R^5$=chlorine):

TABLE 1

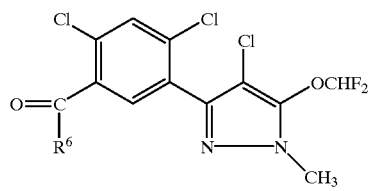

Ia

| No. | $R^6$ |
|---|---|
| Ia.001 | —O—CH$_2$—CH=N—OH |
| Ia.002 | —O—CH$_2$—CH=N—O—CH$_3$ |
| Ia.003 | —O—CH$_2$—CH=N—O—C$_2$H$_5$ |
| Ia.004 | —O—CH$_2$—CH=N—O—CH$_2$—CH$_2$—C$_2$H$_5$ |
| Ia.005 | —O—CH$_2$—CH=N—O—CH$_2$—CH=CH$_2$ |
| Ia.006 | —O—CH$_2$—CH=N—O—CH$_2$—CH=CHCl |
| Ia.007 | —O—CH$_2$—CH=N—O—CH$_2$—CH=CH—CH$_3$ |
| Ia.008 | —O—CH$_2$—CH=N—O—CH$_2$-phenyl |
| Ia.009 | —O—CH$_2$—CH=N—O—CH$_2$-(4-chlorophenyl) |
| Ia.010 | —O—CH$_2$—CH=N—O—CH$_2$-(2-chlorothiophen-5-yl) |
| Ia.011 | —O—CH$_2$—CH=N—O—CH(CH$_3$)-(4-chlorophenyl) |
| Ia.012 | —O—CH$_2$—CH=N—O—CO—CH$_3$ |
| Ia.013 | —O—CH$_2$—CH=N—O—CO-phenyl |
| Ia.014 | —O—CH$_2$—CH=N—O—CO—(4-chlorophenyl) |
| Ia.015 | —O—CH$_2$—CH=N—O—CO—O—C$_2$H$_5$ |
| Ia.016 | —O—CH$_2$—CH=N—O—CO—NH—CH$_3$ |
| Ia.017 | —O—CH$_2$—C(CH$_3$)=N—OH |
| Ia.018 | —O—CH$_2$—C(CH$_3$)=N—O—CH$_3$ |
| Ia.019 | —O—CH$_2$—C(CH$_3$)=N—O—C$_2$H$_5$ |
| Ia.020 | —O—CH$_2$—C(CH$_3$)=N—O—CH$_2$—CH$_2$—C$_2$H$_5$ |
| Ia.021 | —O—CH$_2$—C(CH$_3$)=N—O—CH$_2$—CH=CH$_2$ |
| Ia.022 | —O—CH$_2$—C(CH$_3$)=N—O—CH$_2$—CH=CHCl |
| Ia.023 | —O—CH$_2$—C(CH$_3$)=N—O—CH$_2$—CH=CH—CH$_3$ |
| Ia.024 | —O—CH$_2$—C(CH$_3$)=N—O—CH$_2$-phenyl |
| Ia.025 | —O—CH$_2$—C(CH$_3$)=N—O—CH$_2$-(4-chlorophenyl) |
| Ia.026 | —O—CH$_2$—C(CH$_3$)=N—O—CH$_2$-(2-chlorothiophen-5-yl) |
| Ia.027 | —O—CH$_2$—C(CH$_3$)=N—O—CH(CH$_3$)-(4-chlorophenyl) |

TABLE 1-continued

Ia

| No. | R⁶ |
|---|---|
| Ia.028 | —O—CH₂—C(CH₃)=N—O—CO—CH₃ |
| Ia.029 | —O—CH₂—C(CH₃)=N—O—CO-phenyl |
| Ia.030 | —O—CH₂—C(CH₃)=N—O—CO-(4-chlorophenyl) |
| Ia.031 | —O—CH₂—C(CH₃)=N—O—CO—O—C₂H₅ |
| Ia.032 | —O—CH₂—C(CH₃)=N—O—CO—NH—CH₃ |
| Ia.033 | —O—CH₂—C(CH₃)=N—O—CH₂—CH₂—CH=CH-(4-fluorophenyl) |
| Ia.034 | —O—CH₂—C(CN)=N—O—CH₃ |
| Ia.035 | —O—CH₂—C(CN)=N—O—C₂H₅ |
| Ia.036 | —O—CH₂—C(CN)=N—O—CH₂—CH₂—C₂H₅ |
| Ia.037 | —O—CH₂—C(CN)=N—O—CH₂—CH=CH₂ |
| Ia.038 | —O—CH₂—C(CN)=N—O—CH₂-phenyl |
| Ia.039 | —O—CH₂—C(CN)=N—O—CO—CH₃ |
| Ia.040 | —O—CH₂—C(CN)=N—O—CO-phenyl |
| Ia.041 | —O—CH₂—C(OCH₃)=N—O—CH₃ |
| Ia.042 | —O—CH₂—C(OCH₃)=N—O—C₂H₅ |
| Ia.043 | —O—CH₂—C(OCH₃)=N—O—CH₂—CH₂—C₂H₅ |
| Ia.044 | —O—CH₂—C(OCH₃)=N—O—CH₂—CH=CH₂ |
| Ia.045 | —O—CH₂—C(OCH₃)=N—O—CH₂-phenyl |
| Ia.046 | —O—CH₂—C(OCH₃)=N—O—CO—CH₃ |
| Ia.047 | —O—CH₂—C(OCH₃)=N—O—CO-phenyl |
| Ia.048 | —O—CH₂—C(SCH₃)=N—O—CH₃ |
| Ia.049 | —O—CH₂—C(SCH₃)=N—O—C₂H₅ |
| Ia.050 | —O—CH₂—C(SCH₃)=N—O—CH₂—CH₂—C₂H₅ |
| Ia.051 | —O—CH₂—C(SCH₃)=N—O—CH₂—CH=CH₂ |
| Ia.052 | —O—CH₂—C(SCH₃)=N—O—CH₂-phenyl |
| Ia.053 | —O—CH₂—C(SCH₃)=N—O—CO—CH₃ |
| Ia.054 | —O—CH₂—C(SCH₃)=N—O—CO-phenyl |
| Ia.055 | —O—CH₂—C(phenyl)=N—OH |
| Ia.056 | —O—CH₂—C(phenyl)=N—O—CH₃ |
| Ia.057 | —O—CH₂—C(phenyl)=N—O—C₂H₅ |
| Ia.058 | —O—CH₂—C(phenyl)=N—O—CH₂—CH₂—C₂H₅ |
| Ia.059 | —O—CH₂—C(phenyl)=N—O—CH₂—CH=CH₂ |
| Ia.060 | —O—CH₂—C(phenyl)=N—O—CO—CH₃ |
| Ia.061 | —O—CH₂—C(phenyl)=N—O—CO—O—C₂H₅ |
| Ia.062 | —O—CH₂—C(phenyl)=N—O—CO—NH—CH₃ |
| Ia.063 | —O—CH₂—C(2,4-dichlorophenyl)=N—OH |
| Ia.064 | —O—CH₂—C(2,4-dichlorophenyl)=N—O—CH₃ |
| Ia.065 | —O—CH₂—C(2,4-dichlorophenyl)=N—O—C₂H₅ |
| Ia.066 | —O—CH₂—C(2,4-dichlorophenyl)=N—O—CH₂—CH₂—C₂H₅ |
| Ia.067 | —O—CH₂—C(2,4-dichlorophenyl)=N—O—CH₂—CH=CH₂ |
| Ia.066 | —O—CH₂—C(2,4-dichlorophenyl)=N—O—CO—CH₃ |
| Ia.069 | —O—CH₂—C(2,4-dichlorophenyl)=N—O—CO—O—C₂H₅ |
| Ia.070 | —O—CH₂—C(2,4-dichlorophenyl)=N—O—CO—NH—CH₃ |
| Ia.071 | —S—CH₂—CH=N—OH |
| Ia.072 | —S—CH₂—CH=N—O—CH₃ |
| Ia.073 | —S—CH₂—CH=N—O—C₂H₅ |
| Ia.074 | —S—CH₂—CH=N—O—CH₂—CH=CH₂ |
| Ia.075 | —S—CH₂—CH=N—O—CH₂-phenyl |
| Ia.076 | —S—CH₂—CH=N—O—CO—CH₃ |
| Ia.077 | —S—CH₂—CH=N—O—CO-phenyl |
| Ia.078 | —S—CH₂—CH=N—O—CO—O—C₂H₅ |
| Ia.079 | —S—CH₂—CH=N—O—CO—NH—CH₃ |
| Ia.080 | —S—CH₂—C(CH₃)=N—OH |
| Ia.081 | —S—CH₂—C(CH₃)=N—O—CH₃ |
| Ia.082 | —S—CH₂—C(CH₃)=N—O—C₂H₅ |
| Ia.083 | —S—CH₂—C(CH₃)=N—O—CH₂—CH=CH₂ |
| Ia.084 | —S—CH₂—C(CH₃)=N—O—CH₂-phenyl |
| Ia.085 | —S—CH₂—C(CH₃)=N—O—CO—CH₃ |
| Ia.086 | —S—CH₂—C(CH₃)=N—O—CO-phenyl |
| Ia.087 | —S—CH₂—C(CH₃)=N—O—CO—O—C₂H₅ |
| Ia.088 | —S—CH₂—C(CH₃)=N—O—CO—NH—CH₃ |
| Ia.089 | —S—CH₂—C(CN)=N—O—CH₃ |
| Ia.090 | —S—CH₂—C(CN)=N—O—C₂H₅ |
| Ia.091 | —S—CH₂—C(OCH₃)=N—O—CH₃ |
| Ia.092 | —S—CH₂—C(OCH₃)=N—O—C₂H₅ |

TABLE 1-continued

Ia

[Structure: 2,4-dichlorobenzoyl group with R⁶–C(=O)– attached to a phenyl ring bearing Cl substituents, connected to a pyrazole with Cl, OCHF₂, and N–CH₃ substituents]

| No. | R⁶ |
|---|---|
| Ia.093 | —S—CH₂—C(SCH₃)=N—O—CH₃ |
| Ia.094 | —S—CH₂—C(SCH₃)=N—O—C₂H₅ |
| Ia.095 | —S—CH₂—C(phenyl)=N—O—CH₃ |
| Ia.096 | —S—CH₂—C(phenyl)=N—O—C₂H₅ |
| Ia.097 | —S—CH₂—C(2,4-dichlorophenyl)—CH=N—O—CH₃ |
| Ia.098 | —S—CH₂—C(2,4-dichlorophenyl)-CH=N—O—C₂H₅ |
| Ia.099 | —NH—CH₂—CH=N—OH |
| Ia.100 | —NH—CH₂—CH=N—O—CH₃ |
| Ia.101 | —NH—CH₂—CH=N—O—C₂H₅ |
| Ia.102 | —NH—CH₂—CH=N—O—CH₂—CH=CH₂ |
| Ia.103 | —NH—CH₂—CH=N—O—CH₂-phenyl |
| Ia.104 | —NH—CH₂—CH=N—O—CO—CH₃ |
| Ia.105 | —NH—CH₂—CH=N—O—CO-phenyl |
| Ia.106 | —NH—CH₂—CH=N—O—CO—O—C₂H₅ |
| Ia.107 | —NH—CH₂—CH=N—O—CO—NH—CH₃ |
| Ia.108 | —NH—CH₂—C(CH₃)=N—OH |
| Ia.109 | —NH—CH₂—C(CH₃)=N—O—CH₃ |
| Ia.110 | —NH—CH₂—C(CH₃)=N—O—C₂H₅ |
| Ia.111 | —NH—CH₂—C(CH₃)=N—O—CH₂—CH=CH₂ |
| Ia.112 | —NH—CH₂—C(CH₃)=N—O—CH₂-phenyl |
| Ia.113 | —NH—CH₂—C(CH₃)=N—O—CO—CH₃ |
| Ia.114 | —NH—CH₂—C(CH₃)=N—O—CO-phenyl |
| Ia.115 | —NH—CH₂—C(CH₃)=N—O—CO—O—C₂H₅ |
| Ia.116 | —NH—CH₂—C(CH₃)=N—O—CO—NH—CH₃ |
| Ia.117 | —NH—CH₂—C(CN)=N—O—CH₃ |
| Ia.118 | —NH—CH₂—C(CN)=N—O—C₂H₅ |
| Ia.119 | —NH—CH₂—C(OCH₃)=N—O—CH₃ |
| Ia.120 | —NH—CH₂—C(OCH₃)=N—O—C₂H₅ |
| Ia.121 | —NH—CH₂—C(SCH₃)=N—O—CH₃ |
| Ia.122 | —NH—CH₂—C(SCH₃)=N—O—C₂H₅ |
| Ia.123 | —NH—CH₂—C(phenyl)=N—O—CH₃ |
| Ia.124 | —NH—CH₂—C(phenyl)=N—O—C₂H₅ |
| Ia.125 | —NH—CH₂—C(2,4-dichlorophenyl)—CH=N—O—CH₃ |
| Ia.126 | —NH—CH₂—C(2,4-dichlorophenyl)—CH=N—O—C₂H₅ |
| Ia.127 | —NH—O—CH₂—CH=N—OH |
| Ia.128 | —NH—O—CH₂—CH=N—O—CH₃ |
| Ia.129 | —NH—O—CH₂—CH=N—O—C₂H₅ |
| Ia.130 | —NH—O—CH₂—CH=N—O—CH₂—CH₂—C₂H₅ |
| Ia.131 | —NH—O—CH₂—CH=N—O—CH₂—CH=CH₂ |
| Ia.132 | —NH—O—CH₂—CH=N—O—CH₂—CH=CHCl |
| Ia.133 | —NH—O—CH₂—CH=N—O—CH₂-phenyl |
| Ia.134 | —NH—O—CH₂—CH=N—O—CH₂-(4-chlorophenyl) |
| Ia.135 | —NH—O—CH₂—CH=N—O—CH₂-(4-fluorophenyl) |
| Ia.136 | —NH—O—CH₂—CH=N—O—CH₂-(4-trifluoromethylphenyl) |
| Ia.137 | —NH—O—CH₂—CH=N—O—CH₂-(2,4-dichlorophenyl) |
| Ia.138 | —NH—O—CH₂—CH=N—O—CH₂-(2,4-difluorophenyl) |
| Ia.139 | —NH—O—CH₂—CH=N—O—CH₂—CH₂—O—(4-chlorophenyl) |
| Ia.140 | —NH—O—CH₂—CH=N—O—CH₂—CH₂—O-(4-fluorophenyl) |
| Ia.141 | —NH—O—CH₂—CH=N—O—CH₂—CH₂—O-(3-fluorophenyl) |
| Ia.142 | —NH—O—CH₂—CH=N—O—CH₂—CH(CH₃)—O-(4-chlorophenyl) |
| Ia.143 | —NH—O—CH₂—CH=N—O—CH₂—CH(CH₃)—O-(4-fluorophenyl) |
| Ia.144 | —NH—O—CH₂—CH=N—O—CO—CH₃ |
| Ia.145 | —NH—O—CH₂—CH=N—O—CO-phenyl |
| Ia.146 | —NH—O—CH₂—CH=N—O—CO—O—C₂H₅ |
| Ia.147 | —NH—O—CH₂—CH=N—O—CO—NH—CH₃ |
| Ia.148 | —NH—O—CH₂—C(CH₃)=N—OH |
| Ia.149 | —NH—O—CH₂—C(CH₃)=N—O—CH₃ |
| Ia.150 | —NH—O—CH₂—C(CH₃)=N—O—C₂H₅ |
| Ia.151 | —NH—O—CH₂—C(CH₃)=N—O—CH₂—CH₂—C₂H₅ |
| Ia.152 | —NH—O—CH₂—C(CH₃)=N—O—CH₂—CH=CH₂ |
| Ia.153 | —NH—O—CH₂—C(CH₃)=N—O—CH₂—CH=CHCl |
| Ia.154 | —NH—O—CH₂—C(CH₃)=N—O—CH₂-phenyl |
| Ia.155 | —NH—O—CH₂—C(CH₃)=N—O—CH₂-(4-chlorophenyl) |
| Ia.156 | —NH—O—CH₂—C(CH₃)=N—O—CH₂-(4-fluorophenyl) |
| Ia.157 | —NH—O—CH₂—C(CH₃)=N—O—CH₂-(4-trifluoromethylphenyl) |

TABLE 1-continued

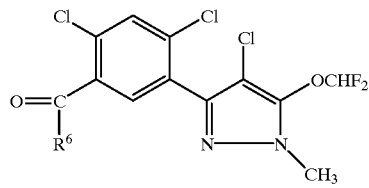

| No. | R⁶ |
|---|---|
| Ia.158 | —NH—O—CH₂—C(CH₃)=N—O—CH₂-(2,4-dichlorophenyl) |
| Ia.159 | —NH—O—CH₂—C(CH₃)=N—O—CH₂-(2,4-difluorophenyl) |
| Ia.160 | —NH—O—CH₂—C(CH₃)=N—O—CH₂—CH₂—O-(4-chlorophenyl) |
| Ia.161 | —NH—O—CH₂—C(CH₃)=N—O—CH₂—CH₂—O-(4-fluorophenyl) |
| Ia.162 | —NH—O—CH₂—C(CH₃)=N—O—CH₂—CH₂—O-(3-fluorophenyl) |
| Ia.163 | —NH—O—CH₂—C(CH₃)=N—O—CH₂—CH(CH₃)—O-(4-chlorophenyl) |
| Ia.164 | —NH—O—CH₂—C(CH₃)=N—O—CH₂—CH(CH₃)—O-(4-fluorophenyl) |
| Ia.165 | —NH—O—CH₂—C(CH₃)=N—O—CO—CH₃ |
| Ia.166 | —NH—O—CH₂—C(CH₃)=N—O—CO-phenyl |
| Ia.167 | —NH—O—CH₂—C(CH₃)=N—O—CO—O—C₂H₅ |
| Ia.168 | —NH—O—CH₂—C(CH₃)=N—O—CO—NH—CH₃ |
| Ia.169 | —NH—O—CH₂—C(C₂H₅)=N—OH |
| Ia.170 | —NH—O—CH₂—C(C₂H₅)=N—O—CH₃ |
| Ia.171 | —NH—O—CH₂—C(C₂H₅)=N—O—C₂H₅ |
| Ia.172 | —NH—O—CH₂—C(C₂H₅)=N—O—CH₂—CH=CH₂ |
| Ia.173 | —NH—O—CH₂—C(C₂H₅)=N—O—CH₂-phenyl |
| Ia.174 | —NH—O—CH₂—C(C₂H₅)=N—O—CH₂-(4-chlorophenyl) |
| Ia.175 | —NH—O—CH₂—C(C₂H₅)=N—O—CO—CH₃ |
| Ia.176 | —NH—O—CH₂—C(C₂H₅)=N—O—CO-phenyl |
| Ia.177 | —NH—O—CH₂—C(C₂H₅)=N—O—CO—O—C₂H₅ |
| Ia.178 | —NH—O—CH₂—C(C₂H₅)=N—O—CO—NH—CH₃ |
| Ia.179 | —O—CH₂—CH₂—CH=N—OH |
| Ia.180 | —O—CH₂—CH₂—CH=N—O—CH₃ |
| Ia.181 | —O—CH₂—CH₂—CH=N—O—C₂H₅ |
| Ia.182 | —O—CH₂—CH₂—CH=N—O—CO—CH₃ |
| Ia.183 | O—CH₂—CH₂—CH=N—O—CO-phenyl |
| Ia.184 | O—CH₂—CH₂—CH=N—O—CO—NH—CH₃ |
| Ia.185 | —O—CH₂—CH₂—C(CH₃)=N—OH |
| Ia.186 | —O—CH₂—CH₂—C(CH₃)=N—O—CH₃ |
| Ia.187 | O—CH₂—CH₂—C(CH₃)=N—O—C₂H₅ |
| Ia.188 | —O—CH₂—CH₂—C(CH₃)=N—O—CO—CH₃ |
| Ia.189 | —O—CH₂—CH₂—C(CH₃)=N—O—CO-phenyl |
| Ia.190 | —O—CH₂—CH₂—C(CH₃)=N—O—CO—NH—CH₃ |
| Ia.191 | —O—CH₂—C(CH₃)₂—CH=N—OH |
| Ia.192 | —O—CH₂—C(CH₃)₂—CH=N—O—CH₃ |
| Ia.193 | —O—CH₂—C(CH₃)₂—CH=N—O—C₂H₅ |
| Ia.194 | —O—CH₂—C(CH₃)₂—CH=N—O—CH₂—CH₂=CH₂ |
| Ia.195 | —O—CH₂—C(CH₃)₂—CH=N—O—CO—CH₃ |
| Ia.196 | —O—CH₂—C(CH₃)₂—CH=N—O—CO-phenyl |
| Ia.197 | —O—CH₂—C(CH₃)₂—CH=N—O—CO—NH—CH₃ |
| Ia.198 | —O—CH₂—O—N=CH—CH₃ |
| Ia.199 | —O—CH₂—O—N=CH—C₂H₅ |
| Ia.200 | —O—CH₂—O—N=CH—CH₂—CH₂—C₂H₅ |
| Ia.201 | —O—CH₂—O—N=CH—CH₂—OCH₃ |
| Ia.202 | —O—CH₂—O—N=CH-(phenyl) |
| Ia.203 | —O—CH₂—O—N=CH-(4-chlorophenyl) |
| Ia.204 | —O—CH₂—O—N=C(CH₃)₂ |
| Ia.205 | —O—CH₂—O—N=C(CH₃)—C₂H₅ |
| Ia.206 | —O—CH₂—O—N=C(CH₃)—CH₂—CH₂—C₂H₅ |
| Ia.207 | —O—CH₂—O—N=C(CH₃)—CH₂—OCH₃ |
| Ia.208 | —O—CH₂—O—N=C(CH₃)-(phenyl) |
| Ia.209 | —O—CH₂—O—N=C(CH₃)-(4-chlorophenyl) |
| Ia.210 | —O—CH₂—O—N=(cyclopentylidene) |
| Ia.211 | —O—CH₂—O—N=(cyclohexylidene) |
| Ia.212 | —O—CH₂—O—N=(cycloheptylidene) |
| Ia.213 | —O—CH₂—O—N=(cyclooctylidene) |
| Ia.214 | —S—CH₂—O—N=CH—CH₃ |
| Ia.215 | —S—CH₂—O—N=CH-(phenyl) |
| Ia.216 | —S—CH₂—O—N=C(CH₃)₂ |
| Ia.217 | —S—CH₂—O—N=(cyclohexylidene) |
| Ia.218 | —NH—CH₂—O—N=CH—CH₃ |
| Ia.219 | —NH—CH₂—O—N=CH-(phenyl) |
| Ia.220 | —NH—CH₂—O—N=C(CH₃)₂ |
| Ia.221 | —NH—CH₂—O—N=(cyclohexylidene) |
| Ia.222 | —NH—O—CH₂—O—N=CH—CH₃ |

TABLE 1-continued

Ia

| No. | R$^6$ |
|---|---|
| Ia.223 | —NH—O—CH$_2$—O—N=CH-(phenyl) |
| Ia.224 | —NH—O—CH$_2$—O—N=C(CH$_3$)$_2$ |
| Ia.225 | —NH—O—CH$_2$—O—N=(cyclohexylidene) |
| Ia.226 | —O—CH$_2$—CH$_2$—O—N=CH—CH$_3$ |
| Ia.227 | —O—CH$_2$—CH$_2$—O—N=CH-(phenyl |
| Ia.228 | —O—CH$_2$—CH$_2$—O—N=C(CH$_3$)$_2$ |
| Ia.229 | —O—CH$_2$—CH$_2$—O—N=(cyclohexylidene) |
| Ia.230 | —S—CH$_2$—CH$_2$—O—N=CH—CH$_3$ |
| Ia.231 | —S—CH$_2$—CH$_2$—O—N=CH-(phenyl) |
| Ia.232 | —S—CH$_2$—CH$_2$—O—N=C(CH$_3$)$_2$ |
| Ia.233 | —S—CH$_2$—CH$_2$—O—N=(cyclohexylidene) |
| Ia.234 | —NH—CH$_2$—CH$_2$—O—N=CH—CH$_3$ |
| Ia.235 | —NH—CH$_2$—CH$_2$—O—N=CH-(phenyl) |
| Ia.236 | —NH—CH$_2$—CH$_2$—O—N=C(CH$_3$)$_2$ |
| Ia.237 | —NH—CH$_2$—CH$_2$—O—N=(cyclohexylidene) |
| Ia.238 | —NH—O—CH$_2$—CH$_2$—O—N=CH—CH$_3$ |
| Ia.239 | —NH—O—CH$_2$—CH$_2$—O—N=CH-(phenyl) |
| Ia.240 | —NH—O—CH$_2$—CH$_2$—O—N=CH-(4-chlorophenyl) |
| Ia.241 | —NH—O—CH$_2$—CH$_2$—O—N=CH-(4-fluorophenyl) |
| Ia.242 | —NH—O—CH$_2$—CH$_2$—O—N=CH-(2,4-dichlorophenyl) |
| Ia.243 | —NH—O—CH$_2$—CH$_2$—O—N=CH-(3,4-difluorophenyl) |
| Ia.244 | —NH—O—CH$_2$—CH$_2$—O—N=C(CH$_3$)$_2$ |
| Ia.245 | —NH—O—CH$_2$—CH$_2$—O—N=(cyclohexylidene) |
| Ia.246 | —O—CH$_2$—SO$_2$—CH$_3$ |
| Ia.247 | —O—CH$_2$—SO$_2$—C$_2$H$_5$ |
| Ia.248 | —O—CH$_2$—SO$_2$—CH$_2$—CH=CH$_2$ |
| Ia.249 | —O—CH$_2$—SO$_2$—CH$_2$-(phenyl) |
| Ia.250 | —O—CH$_2$—SO$_2$-(phenyl) |
| Ia.251 | —O—CH$_2$—SO$_2$-(4-chlorophenyl) |
| Ia.252 | —O—CH$_2$—SO$_2$-(4-methylphenyl) |
| Ia.253 | —O—CH$_2$—SO$_2$-(4-fluorophenyl) |
| Ia.254 | —O—CH$_2$—SO$_2$—C(CH$_3$)$_3$ |
| Ia.255 | —S—CH$_2$—SO$_2$—CH$_3$ |
| Ia.256 | —S—CH$_2$—SO$_2$—C$_2$H$_5$ |
| Ia.257 | —S—CH$_2$—SO$_2$—CH$_2$-(phenyl) |
| Ia.258 | —S—CH$_2$—SO$_2$-(phenyl) |
| Ia.259 | —S—CH$_2$—SO$_2$-(4-methylphenyl) |
| Ia.260 | —NH—CH$_2$—SO$_2$—CH$_3$ |
| Ia.261 | —NH—CH$_2$—SO$_2$—C$_2$H$_5$ |
| Ia.262 | —NH—CH$_2$—SO$_2$—CH$_2$-(phenyl) |
| Ia.263 | —NH—CH$_2$—SO$_2$-(phenyl) |
| Ia.264 | —NH—CH$_2$—SO$_2$-(4-methylphenyl) |
| Ia.265 | —NH—O—CH$_2$—SO$_2$—CH$_3$ |
| Ia.266 | —NH—O—CH$_2$—SO$_2$—C$_2$H$_5$ |
| Ia.267 | —NH—O—CH$_2$—SO$_2$—CH$_2$-(phenyl) |
| Ia.268 | —NH—O—CH$_2$—SO$_2$-(phenyl) |
| Ia.269 | —NH—O—CH$_2$—SO$_2$-(4-methylphenyl) |
| Ia.270 | —O—CH$_2$—CH$_2$—SO$_2$—CH$_3$ |
| Ia.271 | —O—CH$_2$—CH$_2$—SO$_2$—C$_2$H$_5$ |
| Ia.272 | —O—CH$_2$—CH$_2$—SO$_2$—CH$_2$—CH=CH$_2$ |
| Ia.273 | —O—CH$_2$—CH$_2$—SO$_2$—CH$_2$-(phenyl) |
| Ia.274 | —O—CH$_2$—CH$_2$—SO$_2$-(phenyl) |
| Ia.275 | —O—CH$_2$—CH$_2$—SO$_2$-(4-chlorophenyl) |
| Ia.276 | —O—CH$_2$—CH$_2$—SO$_2$-(4-methylphenyl) |
| Ia.277 | —O—CH$_2$—CH$_2$—SO$_2$-(4-fluorophenyl) |
| Ia.278 | —O—CH$_2$—CH$_2$—SO$_2$-(2,4-dichlorophenyl) |
| Ia.279 | —O—CH$_2$—CH$_2$—SO$_2$-(3-trifluoromethylphenyl) |
| Ia.280 | —O—CH$_2$—CH$_2$—SO$_2$-(4-trifluoromethylphenyl) |
| Ia.281 | —O—CH$_2$—CH$_2$—SO$_2$—C(CH$_3$)$_3$ |
| Ia.282 | —S—CH$_2$—CH$_2$—SO$_2$—CH$_3$ |
| Ia.283 | —S—CH$_2$—CH$_2$—SO$_2$—C$_2$H$_5$ |
| Ia.284 | —S—CH$_2$—CH$_2$—SO$_2$—CH$_2$-(phenyl) |
| Ia.285 | —S—CH$_2$—CH$_2$—SO$_2$-(phenyl) |
| Ia.286 | —S—CH$_2$—CH$_2$—SO$_2$-(4-methylphenyl) |
| Ia.287 | —NH—CH$_2$—CH$_2$—SO$_2$—CH$_3$ |

TABLE 1-continued

Ia

| No. | R⁶ |
|---|---|
| Ia.288 | —NH—CH₂—CH₂—SO₂—C₂H₅ |
| Ia.289 | —NH—CH₂—CH₂—SO₂—CH₂-(phenyl) |
| Ia.290 | —NH—CH₂—CH₂—SO₂-(phenyl) |
| Ia.291 | —NH—CH₂—CH₂—SO₂-(4-methylphenyl) |
| Ia.292 | —NH—O—CH₂—CH₂—SO₂—CH₃ |
| Ia.293 | —NH—O—CH₂—CH₂—SO₂—C₂H₅ |
| Ia.294 | —NH—O—CH₂—CH₂—SO₂—CH₂(phenyl) |
| Ia.295 | —NH—O—CH₂—CH₂—SO₂-(phenyl) |
| Ia.296 | —NH—O—CH₂—CH₂—SO₂-(4-methylphenyl) |
| Ia.297 | —O—CH₂-(oxiran-2-yl) |
| Ia.298 | —O—CH₂-(2-methyloxiran-2-yl) |
| Ia.299 | —O—CH₂-(3-methyloxiran-2-yl) |
| Ia.300 | —O—CH₂-(3,3-dimethyloxiran-2-yl) |
| Ia.301 | —O—CH₂—CH₂-(aziridin-1-yl) |
| Ia.302 | —O-(oxetan-3-yl) |
| Ia.303 | —O-(thietan-3-yl) |
| Ia.304 | —O-(1-acetylazetidin-3-yl) |
| Ia.305 | —O-(oxetan-2-yl) |
| Ia.306 | —O—CH₂-(3-methyloxetan-3-yl) |
| Ia.307 | —O—CH₂-(3-ethyloxetan-3-yl) |
| Ia.308 | —O—CH₂-(3-propyloxetan-3-yl) |
| Ia.309 | —O—CH₂—CH₂-(azetidin-1-yl) |
| Ia.310 | —O-(tetrahydrofuran-3-yl) |
| Ia.311 | —O-(3-acetoxytetrahydrofuran-4-yl) |
| Ia.312 | —O-(pyrrolidin-3-yl) |
| Ia.313 | —O-(1-methylpyrrolidin-3-yl) |
| Ia.314 | —O-(1-ethylpyrrolidin-3-yl) |
| Ia.315 | —O-(1-isopropylpyrrolidin-3-yl) |
| Ia.316 | —O-(tetrahydrothiophen-3-yl) |
| Ia.317 | —O-(3-chlorosulfolan-4-yl) |
| Ia.318 | —O-(3-bromosulfolan-4-yl) |
| Ia.319 | —O-(dihydro-2(3H)-furanon-3-yl) |
| Ia.320 | —O-(3-methyldihydro-2(3H)-furanon-3-yl) |
| Ia.321 | —O-(4-methyldihydro-2(3H)-furanon-3-yl) |
| Ia.322 | —O-(dihydro-2(3H)-furanon-4-yl) |
| Ia.323 | —O-(2-pyrrolidon-4-yl) |
| Ia.324 | —O-(4-methyl-2-pyrrolidon-4-yl) |
| Ia.325 | —O—CH₂-(1,3-dioxolan-4-yl) |
| Ia.326 | —O—CH₂-(2,2-dimethyl-1,3-dioxolan-4-yl) |
| Ia.327 | —O—CH₂-(1,3-dioxolan-2-on-4-yl) |
| Ia.328 | —O—CH₂—CH₂-(dihydro-2(3H)-furanon-3-yl) |
| Ia.329 | —O—CH₂—CH₂-(dihydro-2(3H)-furanon-5-yl) |
| Ia.330 | —O—CH₂—CH₂-(pyrrolidin-1-yl) |
| Ia.331 | —O—CH₂—CH₂-(2-pyrrolidon-1-yl) |
| Ia.332 | —O—CH₂—CH₂-(2-pyrrolidon-3-yl) |
| Ia.333 | —O—CH₂—CH₂-(1-methyl-2-pyrrolidon-3-yl) |
| Ia.334 | —O—CH₂—CH₂-(1-ethyl-2-pyrrolidon-3-yl) |
| Ia.335 | —O—CH₂—CH₂-(2-pyrrolidon-5-yl) |
| Ia.336 | —O—CH₂—CH₂-(1-methyl-2-pyrrolidon-5-yl) |
| Ia.337 | —O—CH₂—CH₂-(1-ethyl-2-pyrrolidon-5-yl) |
| Ia.338 | —O—CH₂—CH₂-(tetrahydrofuran-3-yl) |
| Ia.339 | —O—CH₂—CH₂-(1-methylpyrrolidin-2-yl) |
| Ia.340 | —O—CH₂—CH₂-(1,3-dioxolan-2-yl) |
| Ia.341 | —O—CH₂—CH₂-(4-methyl-1,3-dioxolan-2-yl) |
| Ia.342 | —O—CH₂—CH₂-(oxazolidin-3-yl) |
| Ia.343 | —O—CH₂—CH₂-(pyrrolidin-2, 5-dion-1-yl) |
| Ia.344 | —O—CH₂—CH₂-(2-oxazolidinon-3-yl) |
| Ia.345 | —O—CH₂—CH₂-(2-thiazolidinon-3-yl) |
| Ia.346 | —O—CH₂—CH₂-(2-imidazolidinon-3-yl) |
| Ia.347 | —O—CH₂—CH₂-(2-imidazolidinon-3-yl) |
| Ia.348 | —O-(tetrahydro-2H-pyran-2-yl) |
| Ia.349 | —O-(4-methyltetrahydro-2H-pyran-2-yl) |
| Ia.350 | —O-(3-methyltetrahydro-2H-pyran-2-yl) |
| Ia.351 | —O-(3,3-dichlorotetrahydro-2H-pyran-2-yl) |
| Ia.352 | —O-(2-ethyl-4-methyltetrahydro-4H-pyran-4-yl) |

TABLE 1-continued

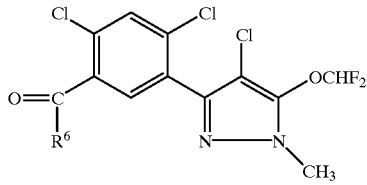

| No. | R$^6$ |
|---|---|
| Ia.353 | —O-(2-isopropyl-4-methyltetrahydro-4H-pyran-4-yl) |
| Ia.354 | —O-(4-methyl-2-tetrahydropyranon-4-yl) |
| Ia.355 | —O-(2-methyl-1,3-dioxan-5-yl) |
| Ia.356 | —O-(2-ethyl-1,3-dioxan-5-yl) |
| Ia.357 | —O-(2-propyl-1,3-dioxan-5-yl) |
| Ia.358 | —O-(2-isopropyl-1,3-dioxan-5-yl) |
| Ia.359 | —O-(2-tert-butyl-1,3-dioxan-5-yl) |
| Ia.360 | —O-(1-methylpiperidin-4-yl) |
| Ia.361 | —O-(2,2,6,6-tetramethylpiperidin-4-yl) |
| Ia.362 | —O-(1-methylpiperidin-3-yl) |
| Ia.363 | —O-(1-ethylpiperidin-3-yl) |
| Ia.364 | —O-(tetrahydrothiopyran-3-yl) |
| Ia.365 | —O—CH$_2$-(tetrahydro-4H-pyran-4-yl) |
| Ia.366 | —O—CH$_2$-(tetrahydro-4H-pyran-3-yl) |
| Ia.367 | —O—CH$_2$-(tetrahydro-2H-pyran-2-yl) |
| Ia.368 | —O—CH$_2$-(5,5-dimethyl-1,3-dioxan-2-yl) |
| Ia.369 | —O—CH$_2$-(5-methyl-1,3-dioxan-5-yl) |
| Ia.370 | —O—CH$_2$-(5-ethyl-1,3-dioxan-5-yl) |
| Ia.371 | —O—CH$_2$-(1-methylpiperidin-3-yl) |
| Ia.372 | —O—CH$_2$-(1-methylpiperidin-2-yl) |
| Ia.373 | —O—CH$_2$-(1,4-dimethylpiperazin-2-yl) |
| Ia.374 | —O—CH$_2$—CH$_2$-(tetrahydro-4H-pyran-4-yl) |
| Ia.375 | —O—CH$_2$—CH$_2$-(piperidin-2-yl) |
| Ia.376 | —O—CH$_2$—CH$_2$-(piperidin-1-yl) |
| Ia.377 | —O—CH$_2$—CH$_2$-(4-methylpiperzain-1-yl) |
| Ia.378 | —O—CH$_2$—CH$_2$-(4-ethoxycarbonylpiperazin-1-yl) |
| Ia.379 | —O—CH$_2$—CH$_2$-(morpholin-4-yl) |
| Ia.380 | —O—CH$_2$—CH$_2$-(2,6-dimethylmorpholin-4-yl) |
| Ia.381 | —O—CH$_2$—CH$_2$-(5,5-dimethyl-1,3-dioxan-2-yl) |
| Ia.382 | —O—CH$_2$—CH$_2$-(hexahydro-1,3,5-triazin-2-thion-5-yl) |
| Ia.383 | —O—CH$_2$—CH$_2$-(1,1-dioxotetrahydro-4H-1,4-thiazin-4-yl) |
| Ia.384 | —O—CH$_2$—CH$_2$-(5,5-dimethyl-1,3-dithian-2-yl) |
| Ia.385 | —O—CH$_2$—CH(CH$_3$)-(1,3-dioxan-2-yl) |
| Ia.386 | —O-(1-methylhexahydroazepin-4-yl) |
| Ia.387 | —O-(oxepan-2-on-5-yl) |
| Ia.388 | —O-(1,4-dithiepan-6-yl) |
| Ia.389 | —O—CH$_2$—CH$_2$-(hexahydroazepin-1-yl) |
| Ia.390 | —S—CH$_2$-(oxiran-2-yl) |
| Ia.391 | —S—CH$_2$—CH$_2$-(aziridin-1-yl) |
| Ia.392 | —S—(oxetan-3-yl) |
| Ia.393 | —S—CH$_2$-(3-methyloxetan-3-yl) |
| Ia.394 | —S—(tetrahydrofuran-3-yl) |
| Ia.395 | —S—(1-methylpyrrolidin-3-yl) |
| Ia.396 | —S—CH$_2$-(1,3-dioxolan-4-yl) |
| Ia.397 | —S—CH$_2$-(imidazolidin-2,5-dion-4-yl) |
| Ia.398 | —S—CH$_2$—CH$_2$-(2-pyrrolidon-1-yl) |
| Ia.399 | —S—CH$_2$—CH$_2$-(1-methyl-2-pyrrolidon-3-yl) |
| Ia.400 | —S—CH$_2$—CH$_2$-(2-pyrrolidon-5-yl) |
| Ia.401 | —S—CH$_2$—CH$_2$-(1,3-dioxolan-2-yl) |
| Ia.402 | —S—CH$_2$—CH$_2$-(1,3-dithiolan-2-yl) |
| Ia.403 | —S—CH$_2$—CH$_2$-(2-oxazolidinon-3-yl) |
| Ia.404 | —S—CH$_2$-(tetrahydro-4H-pyran-4-yl) |
| Ia.405 | —S—CH$_2$-(tetrahydro-4H-pyran-3-yl) |
| Ia.406 | —S—CH$_2$-(tetrahydro-2H-pyran-2-yl) |
| Ia.407 | —S—CH$_2$-(5,5-dimethyl-1,3-dioxan-2-yl) |
| Ia.408 | —S—CH$_2$—CH$_2$-(piperidin-1-yl) |
| Ia.409 | —S—CH$_2$—CH$_2$-(morpholin-4-yl) |
| Ia.410 | —S—CH$_2$—CH$_2$-(hexahydroazepin-1-yl) |
| Ia.411 | —NH—CH$_2$-(oxiran-2-yl) |
| Ia.412 | —NH—CH$_2$—CH$_2$-(aziridin-1-yl) |
| Ia.413 | —NH-(oxetan-3-yl) |
| Ia.414 | —NH-(thietan-3-yl) |
| Ia.415 | —NH-(1-acetylazetidin-3-yl) |
| Ia.416 | —NH—CH$_2$-(oxetan-3-yl) |
| Ia.417 | —NH—CH$_2$—CH$_2$-(azetidin-1-yl) |

TABLE 1-continued

Ia

| No. | R⁶ |
|---|---|
| Ia.418 | —NH-(tetrahydrofuran-3-yl) |
| Ia.419 | —N(CH₃)-(1-methylpyrrolidin-3-yl) |
| Ia.420 | —N(C₂H₅)-(1-ethylpyrrolidin-3-yl) |
| Ia.421 | —NH-(1-methylpyrrolidin-3-yl) |
| Ia.422 | —NH-(tetrahydrothiophen-3-yl) |
| Ia.423 | —NH-(sulfolan-3-yl) |
| Ia.424 | —NH-(3-chlorosulfolan-4-yl) |
| Ia.425 | —NH-(dihydro-2(3H)-furanon-3-yl) |
| Ia.426 | —NH-(dihydro-(3H)-thiophen-2-on-3-yl) |
| Ia.427 | —NH-(dihydro-2(3H)-furanon-4-yl) |
| Ia.428 | —NH-(2-pyrrolidon-4-yl) |
| Ia.429 | —NH—CH₂-(1,3-dioxolan-4-yl) |
| Ia.430 | —NH—CH₂-(2, 2-dimethyl-1,3-dioxolan-4-yl) |
| Ia.431 | —NH—CH₂-(2-methyl-1,3-dioxolan-4-yl) |
| Ia.432 | —NH—CH₂-(2-isopropyl-1,3-dioxolan-4-yl) |
| Ia.433 | —NH—CH₂—CH₂-(dihydro-2(3H)-furanon-3-yl) |
| Ia.434 | —NH—CH₂—CH₂-(pyrrolidin-1-yl) |
| Ia.435 | —NH—CH₂—CH(CH₃)-(2-pyrrolidon-1-yl) |
| Ia.436 | —N(CH₃)—CH₂—CH(CH₃)-(2-pyrrolidon-l-yl) |
| Ia.437 | —NH—CH₂—CH₂-(2-pyrrolidon-3-yl) |
| Ia.438 | —NH—CH₂—CH₂-(1-methylpyrrolidin-2-yl) |
| Ia.439 | —NH—CH₂—CH₂-(1-ethylpyrrolidin-2-yl) |
| Ia.440 | —NH—CH₂—CH₂-(1,3-dioxolan-2-yl) |
| Ia.441 | —N(CH₃)—CH₂—CH₂-(1,3-dioxolan-2-yl) |
| Ia.442 | —NH—CH₂—CH₂-(oxazolidin-3-yl) |
| Ia.443 | —NH-(4-methyltetrahydro-4H-pyran-4-yl) |
| Ia.444 | —NH-(2,4-dimethyltetrahydro-4H-pyran-4-yl) |
| Ia.445 | —NH-(2-ethyl-4-methyltetrahydro-4H-pyran-4-yl) |
| Ia.446 | —NH-(1-methylpiperidin-4-yl) |
| Ia.447 | —N(CH₃)-(1-methylpiperidin-4-yl) |
| Ia.448 | —NH-(1-ethoxycarbonylpiperidin-4-yl) |
| Ia.449 | —NH-(2,2,6,6-tetramethylpiperidin-4-yl) |
| Ia.450 | —NH-(1-ethylpiperidin-3-yl) |
| Ia.451 | —NH—CH₂-(tetrahydro-4H-pyran-4-yl) |
| Ia.452 | —NH—CH₂-(4-methyltetrahydro-4H-pyran-3-yl) |
| Ia.453 | —NH—CH₂-(2,5-dimethyltetrahydro-2H-pyran-2-yl) |
| Ia.454 | —NH—CH₂-(5,5-dimethyl-1,3-dioxan-2-yl) |
| Ia.455 | —NH—CH₂-(1,4-dioxan-2-yl) |
| Ia.456 | —N(CH₃)—CH₂-(1,4-dioxan-2-yl) |
| Ia.457 | —NH—CH₂-(piperidin-4-yl) |
| Ia.458 | —NH—CH₂-(piperidin-2-yl) |
| Ia.459 | —NH—CH₂-(5-methylpiperazin-2-yl) |
| Ia.460 | —NH—CH₂—CH₂-(piperidin-2-yl) |
| Ia.461 | —NH—CH₂—CH₂-(piperidin-1-yl) |
| Ia.462 | —NH—CH₂—CH₂-(4-methylpiperazin-1-yl) |
| Ia.463 | —NH—CH₂—CH₂-(morpholin-4-yl) |
| Ia.464 | —NH—CH₂—CH(C₂H₅)-(4-methyl-1,3-dioxan-2-yl) |
| Ia.465 | —NH-(hexahydroazepin-2-on-3-yl) |
| Ia.466 | —NH—CH₂—CH₂-(hexahydroazepin-1-yl) |
| Ia.467 | —NH—O—CH₂-(oxiran-2-yl) |
| Ia.468 | —NH—O-(dihydro-2(3H)-furanon-3-yl) |
| Ia.469 | —NH—O—CH₂-(tetrahydrofuran-2-yl) |
| Ia.470 | —NH—O—CH₂-(1,3-dioxolan-4-yl) |
| Ia.471 | —NH—O—CH₂—CH₂-(2-pyrrolidon-1-yl) |
| Ia.472 | —NH—O—CH₂—CH₂-(4-methyl-1,3-dioxolan-2-yl) |
| Ia.473 | —NH—O—CH₂—CH₂-(2-oxazolidinon-3-yl) |
| Ia.474 | —NH—O—CH₂-(tetrahydro-2H-pyran-2-yl) |
| Ia.475 | —NH—O—CH₂—CH₂-(piperidin-1-yl) |
| Ia.476 | —NH—O—CH₂—CH₂-(morpholin-4-yl) |
| Ia.477 | —NH—O—CH₂—CH₂-(hexahydroazepin-1-yl) |
| Ia.478 | —O—CH₂-(1,3-dioxolan-2-yl) |
| Ia.479 | —S—CH₂-(1,3-dioxolan-2-yl) |
| Ia.480 | —NH—CH₂-(1,3-dioxolan-2-yl) |
| Ia.481 | —NH—O—CH₂-(1,3-dioxolan-2-yl) |

Furthermore, the 5-pyrazolylbenzoic acid derivatives of the formula Ib are particularly preferred, in particular the compounds Ib.001–Ib.481, which only differ from the corresponding compounds Ia.001–Ia.481 by the fact that $R^4$ is fluorine:

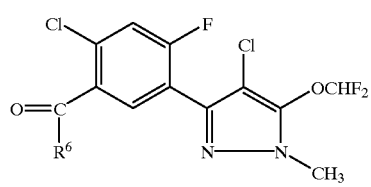

Ib

The 5-pyrazolylbenzoic acid derivatives of the formula I can be obtained by various routes, in particular by one of the processes below:

A) A β-ketocarboxylic acid derivate IV is reacted with hydrazine or with a hydrazine derivate in an inert solvent (cf., for example, JP-A 04/225 937 and JP-A 03/072 460) and the process product V is alkylated:

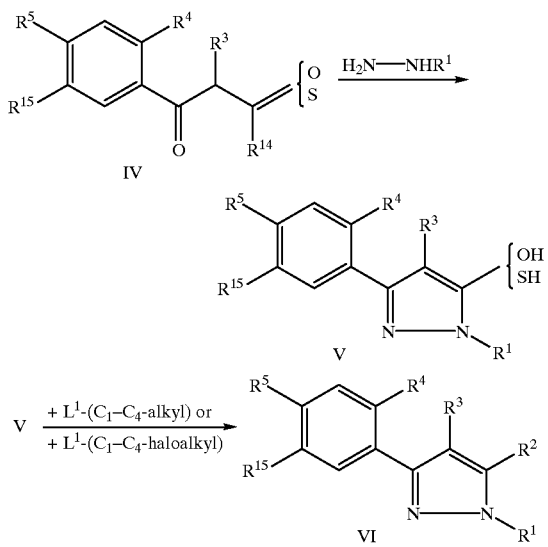

$L^1$ is a customary leaving group, such as halogen, $-O-SO_2CH_3$, $-O-SO_2CF_3$, $-O-SO_2C_4F_9$ and $-O-SO_2(p-CH_3-C_6H_4)$;

$R^{14}$ is preferably halogen, $C_1-C_4$-alkoxy or $(C_1-C_4$-alkyl) carbonyloxy;

$R^{15}$ is hydrogen, nitro, amino, halogen, alkyl, haloalkyl, $-CH_2-R^6$, formyl, carboxyl, alkoxycarbonyl or $-CO-R^6$.

The solvent can be aprotic or protic. Examples of suitable solvents are organic acids, such as acetic acid, hydrocarbons, halogenated hydrocarbons, ethers, such as ethylene glycol dimethyl ether, alcohols, such as methanol and ethanol, and sulfoxides. However, the process can also be carried out in the absence of a solvent.

The reaction temperature is predetermined mainly by the melting point of the solvent or the compound IV and the boiling point of the reaction mixture. The process is preferably carried out at from approximately 60 to 120° C.

In general, approximately 0.95 to 5 times the molar amount, preferably 1 to 1.4 times the amount, of hydrazine or hydrazine derivative, based on the β-ketocarboxylic acid derivative IV, is employed.

The amount of alkylating agent $L^1$-($C_1-C_4$-alkyl) or $L^1$-($C_1-C_4$-haloalkyl) is conventionally also 0.95 to 5 times the molar amount based on the intermediate V.

With a view to the preferred radicals $R^1$ on the 3-phenylpyrazoles I, particularly preferred hydrazine derivatives are those which have an alkyl group attached to them.

The alkylation is conventionally carried out using the halide, preferably the chloride or bromide, or using the sulfate of an alkane or haloalkane, if desired in the presence of an organic base, e.g. a trialkylamine, or of pyridine, or of an inorganic base, for example of an alkali metal carbonate.

The alkylation is expediently carried out in an inert organic solvent, e.g. in an aliphatic or cyclic ether, such as 1,2-dimethoxyethane, tetrahydrofuran and dioxane, in an aliphatic ketone, such as acetone, in an amide, such as dimethylformamide, in a sulfoxide, such as dimethyl sulfoxide, or in a mixture of one of these solvents and water.

The reaction can generally be carried out at from 0° C. to the boiling point of the reaction mixture, preferably at approximately 20 to 80° C.

B) The compounds VI where $R^3$=hydrogen are halogenated:

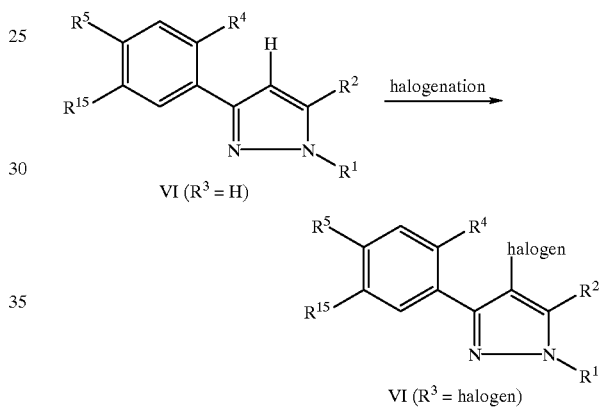

The reaction can be carried out in an inert solvent/diluent, or in the absence of a solvent.

Examples of suitable solvents are organic acids, inorganic acids, hydrocarbons, halogenated hydrocarbons, aromatic hydrocarbons, ethers, sulfides, sulfoxides and sulfones.

Suitable halogenating agents are, for example, chlorine, bromine, N-bromosuccinimide, N-chlorosuccinimide or sulfuryl chloride. Depending on the starting compound and the halogenating agent, an addition of a free-radical initiator, for example an organic peroxide, such as dibenzoyl peroxide, or an azo compound, such as azobisisobutyronitrile, or irradiation with light, may have an advantageous effect on the course of the reaction.

The amount of halogenating agent is not critical. Both substoichiometric amounts and large excesses of halogenating agent, based on the compound VI to be halogenated, where $R^3$ hydrogen, are possible.

If a free-radical initiator is used, a catalytic amount will usually suffice.

The reaction temperature is normally at from (−100) to 200° C., mostly at from 10 to 100° C., or the boiling point of the reaction mixture.

C) 3-(3-Methylphenyl)pyrazoles VI ($R^{15}$=CH$_3$) are halogenated and a) the process products are subjected to nucleophilic substitution followed by oxidation, or b) the process products are hydrolyzed:

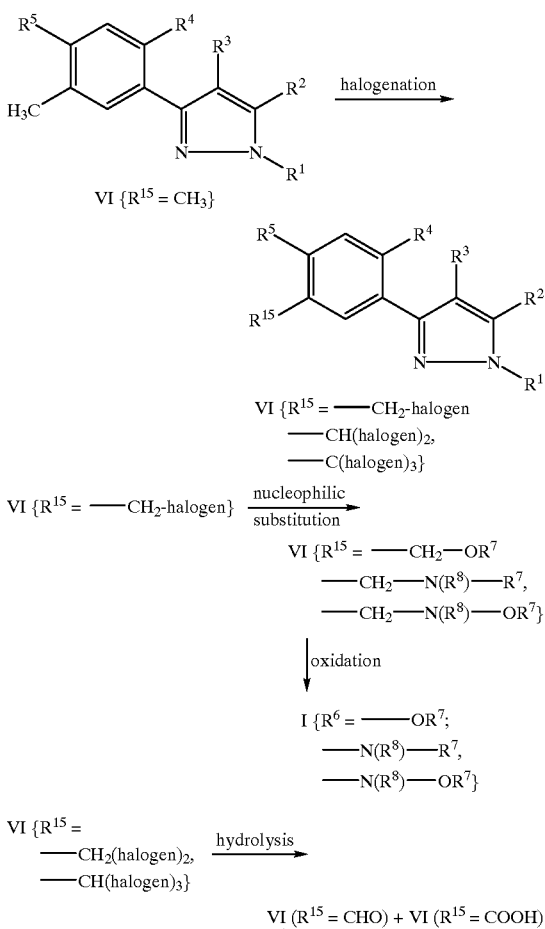

As regards the solvents, the amounts used and the reaction conditions for the halogenation, reference is made to the information given for method B).

In the halogenated compounds VI where $R^{15}$=halomethyl, the halogen atom can be subjected to nucleophilic substitution with an alcohol (—O—$R^7$) or an amine radical (—N($R^8$)—$R^7$ or —N($R^8$)—O—$R^7$).

The nucleophiles used are either the corresponding alcohols or amines, in which case the process is preferably carried out in the presence of a base (e.g. an alkali metal hydroxide, alkaline earth metal hydroxide, alkali metal carbonate or alkaline earth metal carbonate), or else the alkali metal salts of these compounds are used which are obtained by reacting the alcohols or amines with a base (e.g. an alkali metal hydride).

Suitable solvents are, mainly, aprotic organic solvents, e.g. tetrahydrofuran, dimethylformamide, dimethyl sulfoxide, or hydrocarbons, such as toluene and hexane.

The reaction is carried out at between the melting point and the boiling point of the reaction mixture, preferably at from 0 to 100° C.

The substitution products can be converted into the corresponding 5-pyrazolylbenzoic acid derivatives I ($R^6$=—O—$R^7$, —N($R^8$)—$R^7$ or —N($R^8$)—O—$R^7$) by oxidation in a manner known per se {see, for example, Houben-Weyl, Methoden der Organischen Chemie [Methods in Organic Chemistry], Vol. E5, Georg Thieme Verlag, Stuttgart 1985, p. 935 et seq.; S. J. Angyal, K. James, Carbohydr. Res. 12, 147 (1970); P. F. Schuda, M. B. Cichowicz, M. R. Heimann, Tetrahedron Lett. 24, 3829 (1983); ibid. 24, 4267 (1983)}.

Suitable oxidants for this purpose are, preferably, the transition metal compounds, e.g. oxides of chromium, rhodium or ruthenium, preferably in a catalytic to stoichiometric amount based on the compound VI to be oxidized. When catalytic amounts are used, additional oxidants are required, for example oxygen, amine N-oxides or alkali metal periodates, in stoichiometric amounts, or else in an excess, e.g. for achieving particularly high conversion rates.

Suitable solvents are, besides the customary organic solvents, organic acids. The oxidation can also be carried out in an aqueous-organic two-phase system, preferably in the presence of a phase transfer catalyst.

As a rule, the reaction temperature is between the melting point and the boiling point of the reaction mixture, preferably at from 0 to 100° C.

The compounds VI where $R^{15}$=dihalo- or trihalomethyl are preferably hydrolyzed under acidic conditions, for example in the absence of a solvent in hydrochloric acid, acetic acid, formic acid or sulfuric acid, or else in aqueous solutions of these.

As a rule, the hydrolysis is carried out at between the melting point and the boiling point of the reaction mixture, preferably at from 0 to 10° C.

The hydrolysis products VI where $R^{15}$=formyl can be oxidized in a manner known per se to give the corresponding carboxylic acids (see, in this context, in particular pages 179 to 181 of A. H. Haines, "Methods for the Oxidation of Organic Compounds", Academic Press, 1988).

D) "Sandmeyer" reaction of anilines VI ($R^{15}$=NH$_2$) in a manner known per se {see, e.g., Houben-Weyl, "Methoden der Organischen Chemie" [Methods in Organic Chemistry], Vol. 5/4, Georg Thieme Verlag, Stuttgart 1960, p. 438 et seq.}:

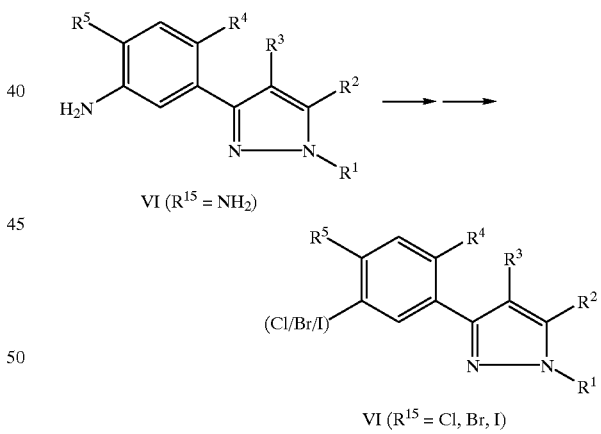

In general, the diazonium salt is obtained in a manner known per se by reacting the aniline VI ($R^{15}$=NH$_2$) with a nitrite, such as sodium nitrite or potassium nitrite, in an aqueous solution of an acid, e.g. in hydrochloric acid, hydrobromic acid or sulfuric acid.

However, it is also possible to carry out the process under anhydrous conditions, e.g. in hydrogen-chloride-containing glacial acetic acid, in absolute alcohol, in dioxane or tetrahydrofuran, in acetonitrile or in acetone, in which case the aniline VI ($R^{15}$=NH$_2$) is treated with a nitrous ester, such as tert-butyl nitrite and isopentyl nitrite.

Particularly preferably, the resulting diazonium salt is converted into the halogen compound VI where $R^{15}$= chlorine, bromine or iodine by treating it with a solution or suspension of a copper(I) salt, such as copper(I) chloride, copper(I) bromide and copper(I) iodide, or with an alkali metal salt solution.

This reaction of the diazonium salt can be effected, for example, in water, in aqueous hydrochloric acid or hydrobromic acid, in a ketone, such as acetone, diethyl ketone and methyl ethyl ketone, in a nitrite, such as acetonitrile, in an ether, such as dioxane and tetrahydrofuran, or in an alcohol, such as methanol and ethanol.

The reaction temperature is normally at from (−30) to +50° C.

Preferably, all reactants are employed in approximately stoichiometric amounts, but an excess of one or the other component may be advantageous.

The anilines VI where $R^{15}$=amino can be obtained by reducing the corresponding nitro compounds VI where $R^{15}$=nitro:

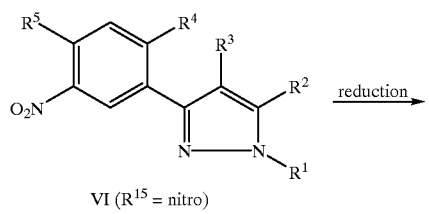

VI ($R^{15}$ = nitro)

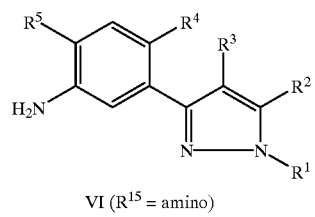

VI ($R^{15}$ = amino)

The reduction can be carried out with a metal, such as iron, zinc or tin, under acetic reaction conditions, or with a complex hydride, such as lithium aluminum hydride and sodium borohydride, suitable solvents—depending on the reducing agent selected—being, e.g., water, alcohols, such as methanol, ethanol and isopropanol, or ethers, such as diethyl ether, methyl tert-butyl ether, dioxane, tetrahydrofuran and ethylene glycol dimethyl ether.

When carrying out the reduction with a metal, the process is preferably carried out in the absence of a solvent in an inorganic acid, in particular in concentrated or dilute hydrochloric acid, or in an organic acid, such as acetic acid. However, it is also possible to admix an inert solvent, e.g. one of those mentioned above, to the acid.

The starting compound VI ($R^{15}$=NO$_2$) and the reducing agent are expediently employed in approximately equimolar amounts; however, to optimize the course of the reaction, it may be advantageous to use one of the two components in an excess, approximately up to 10 times the molar amount.

The amount of acid is not critical. In order to reduce the starting compound as completely as possible, it is expedient to use at least an equivalent amount of acid.

The reaction temperature is generally from (−30) to 200° C., preferably 0 to 80° C.

For working up, the reaction mixture is usually diluted with water and the product isolated by filtration, crystallization or extraction with a solvent which is largely immiscible with water, e.g. with ethyl acetate, diethyl ether or methylene chloride. If desired, the product can subsequently be purified as usual.

The nitro group of the nitrophenylpyrazoles VI ($R^{15}$=nitro) can also be subjected to catalytic hydrogenation by means of hydrogen. Catalysts which are suitable for this purpose are, for example, Raney nickel, palladium-on-charcoal, palladium oxide, platinum and platinum oxide, an amount of 0.05 to 10.0 mol % of catalyst based on the compound to be reduced generally being sufficient.

The process is carried out either in the absence of a solvent or in an inert solvent or diluent, e.g. in acetic acid, in a mixture of acetic acid and water, ethyl acetate, ethanol or in toluene.

After the catalyst has been removed, the reaction solution can be worked up in the usual way to give the product.

The hydrogenation can be carried out under atmospheric pressure or under elevated pressure.

The nitro compounds VI where $R^{15}$=nitro are, in turn, preferably accessible by nitrating phenylpyrazoles VI where $R^{15}$=H:

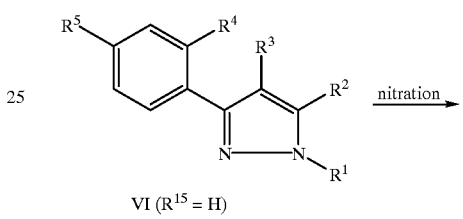

VI ($R^{15}$ = H)

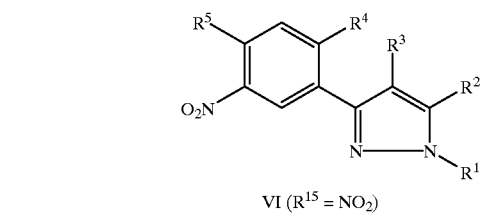

VI ($R^{15}$ = NO$_2$)

Suitable nitration reagents are, for example, nitric acid in various concentrations, or else concentrated and fuming nitric acid, mixtures of sulfuric acid and nitric acid, acetyl nitrates and alkyl nitrates.

The reaction can be carried out either in the absence of a solvent in an excess of the nitrating reagent or in an inert solvent or diluent, suitable solvents or diluents being, e.g., water, mineral acids, organic acids, chlorohydrocarbons, such as methylene chloride, anhydrides, such as acetic anhydride, and mixtures of these.

Starting compound VI ($R^{15}$=H) and nitrating reagent are expediently employed in approximately equimolar amounts; however, to optimize the conversion rate of compound to be nitrated, it may be advantageous to use the nitrating reagent in an excess, approximately up to 10 times the molar amount. If the reaction is carried out in the absence of a solvent in the nitrating reagent, the latter will be present in an even larger excess.

The reaction temperature is normally from (−100) to 200° C., preferably from (−30) to 50° C.

E) Synthesis of esters, amides, thioesters and hydroxamic esters I from carboxylic acids VI where $R^{15}$=COOH in a manner known per se:

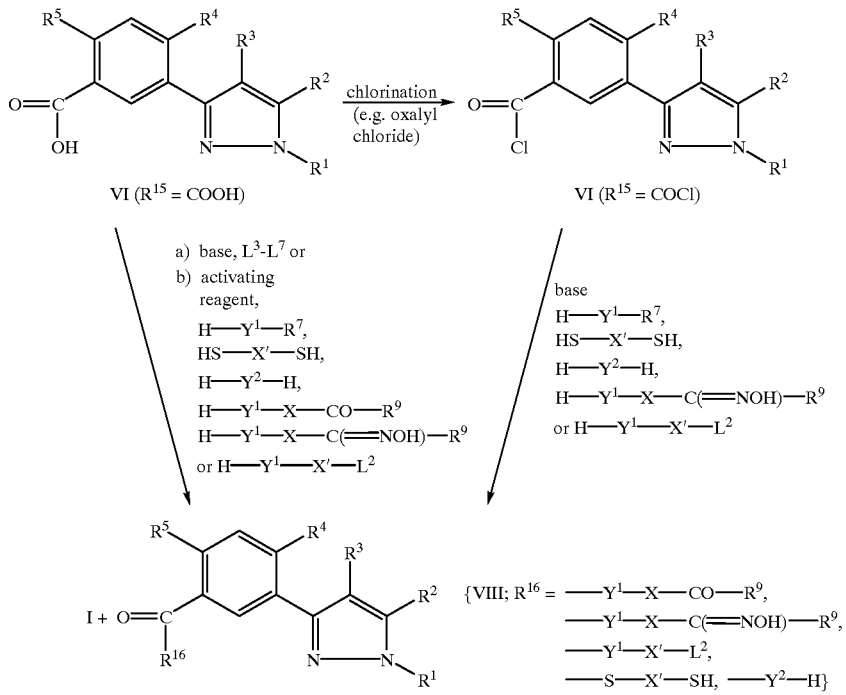

$Y^1$ is —O—, —S—, —N($R^8$)—, —N($R^8$)—O—;
$Y^2$ is —S—, —N($R^8$)—, —N($R^8$)—O—;
X' is a radical X as defined, with the exception of methylene and substituted methylene;
$L^2$ and $L^3$ are customary leaving groups, such as halogen, —O—$SO_2CH_3$, —O—$SO_2CF_3$, —O—$SO_2C_4F_9$ or —O—$SO_2$-(4-methylphenyl).

The reactions are carried out in a manner known per se {see, for example, Houben-Weyl, Methoden der Organischen Chemie [Methods in Organic Chemistry], Georg Thieme Verlag, Stuttgart, Vol. 8, 4th Edition 1952, p. 471 et seq., p. 655 et seq. and p. 686 et seq.; Vol. 9, 1955, p. 753 et seq. and p. 745 et seq.; Vol. E5, 1985, p. 941 et seq.}. For example, the carboxylic acids VI where $R^{15}$=COOH can be converted into their acid chlorides VII, from which the 5-pyrazolylbenzoic acid derivatives I and the compounds VIII are accessible by reaction with suitable alcohols, amines, thiols or alkoxyamines. On the other hand, the carboxylic acids VI ($R^{15}$=COOH) can also be reacted directly with alcohols, amines, thiols or alkoxyamines. In this context, the presence of an activating reagent, e.g. N,N'-dicyclohexylcarbodiimide or carbonyldiimidazolide, may be advantageous. Finally, it is also possible to alkylate carboxylic acids VI ($R^{15}$=COOH) with compounds $R^7$–$L^3$ to give the corresponding esters I ($R^6$=—O—$R^7$).

The 3-phenylpyrazoles VIII can subsequently be converted into the compounds I in a manner known per se. For example, those compounds VIII where $R^{16}$=—$Y^1$—X—CO—$R^9$ react with hydroxylamines $H_2N$—O—Z—$R^{10}$ to give oximes I ($R^6$=—$Y^1$—X—C($R^9$)=N—O—Z—$R^{10}$) (cf., for example, Houben-Weyl, Methoden der Organischen Chemie [Methods in Organic Chemistry], Georg Thieme Verlag, Stuttgart 1968, Vol. 10/4, p. 10 et seq., and Vol. E14b, Stuttgart 1990, p. 290 et seq.). Oximes, thioles, thioacids, acid amides and hydroxamic acids VIII ($R^{16}$=—$Y^1$—X—C(=N—OH)—$R^9$, —S—X'—SH and —$Y^2$—H) can be converted into compounds I by means of alkylation (cf., for example, Houben-Weyl, Methoden der Organischen Chemie [Methods in Organic Chemistry], Georg Thieme Verlag, Vol. E5, Stuttgart 1985, p. 934 et seq. and p. 1148 et seq., and Vol. 9, 4th Edition 1955, p. 749 et seq.), and the thiols VIII ($R^{16}$=—S—$Y^3$—SH) can be converted into thioethers VIII ($R^{16}$=—S—X'—S—Z—$R^{13}$), and these can be oxidized to give sulfones I ($R^6$=—S—X'—$SO_2$—Z—$R^{13}$) (cf., in this context, for example Houben-Weyl, Methoden der Organischen Chemie [Methods in Organic Chemistry], Georg Thieme Verlag, Stuttgart, Vol. 9, 4th Edition 1955, p. 103 et seq. and p. 227 et seq.). Moreover, sulfones I ($R^6$=—$Y^1$—X—$SO_2$—Z—$R^{13}$) are accessible by reacting the compounds VIII ($R^{16}$=—CO—$Y^1$—X—$L^2$) with thiols SH—Z—$R^{13}$, followed by oxidation.

The carboxylic acids VI where $R^{15}$=COOH, in turn, are preferably accessible by carboxylating the halogen compounds VI where $R^{15}$=chlorine, bromine or iodine in a manner known per se (cf., for example, JP-A 06/073 015):

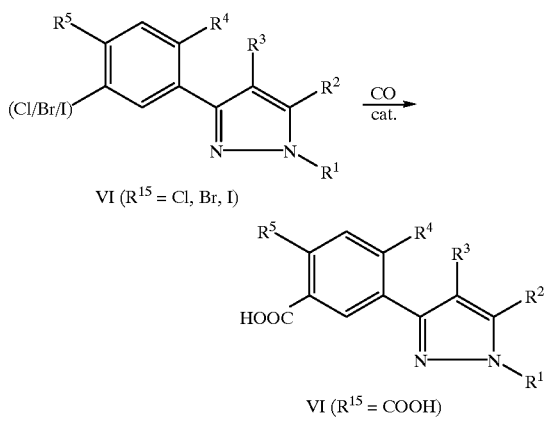

It is expedient to carry out the process in the presence of catalytic amounts of a transition metal complex, preferably a phosphine complex of palladium, under a carbon monoxide pressure of approximately 1 to 100 bar.

As a rule, the reaction is carried out in an inert organic solvent which is miscible with water, e.g. in acetonitrile or in tetrahydrofuran.

Normally, water and an organic or inorganic base such as, in particular, sodium carbonate, are used in approximately equivalent amounts or in an excess of approximately up to 10 times the molar amount based on the amount of starting compound VI (where $R^{15}$=chlorine, bromine or iodine).

The reaction temperature is usually from the melting point of the reaction mixture to approximately 200° C.

Unless otherwise specified, the above-described reactions are expediently carried out under atmospheric pressure or under the inherent pressure of the reaction mixture in question.

As a rule, the reaction mixtures are worked up by methods known per se, for example by diluting the reaction solution with water followed by isolation of the product by means of filtration, crystallization or solvent extraction, or by removing the solvent, partitioning the residue in a mixture of water and a suitable organic solvent and working up the organic phase to obtain the product.

During their preparation, the 5-pyrazolylbenzoic acid derivatives I may be obtained in the form of isomer mixtures, but, if desired, these can be separated by the methods customary for this purpose, such as crystallization or chromatography, for example on an optically active adsorbate, to give the pure isomers. Pure optically active isomers can be prepared advantageously from corresponding optically active starting materials.

Agriculturally useful salts of the compounds I can be formed by reacting them with a base of the corresponding cation, preferably an alkali metal hydroxide or hydride, or by reacting them with an acid of the corresponding anion, preferably of hydrochloric acid, hydrobromic acid, sulfuric acid, phosphoric acid or nitric acid.

Salts of I whose metal ion is not an alkali metal ion can also be prepared by subjecting the corresponding alkali metal salt to double decomposition in the customary manner, and also ammonium, phosphonium, sulfonium and sulfoxonium salts by means of ammonia and phosphonium, sulfonium or sulfoxonium hydroxides.

The compounds I and their agriculturally useful salts are suitable for use as herbicides, either in the form of the isomer mixtures or in the form of the pure isomers. The herbicidal compositions comprising I effect very efficient control of vegetation on non-crop areas, in particular at high rates of application. They act against broad-leaf weeds and grass weeds in crops such as wheat, rice, maize, soya and cotton, without harming the crop plants to a significant extent. This effect is particularly pronounced at low rates of application.

Depending on the method of application in question, the compounds I, or herbicidal compositions comprising them, can also be employed in a further number of crop plants for eliminating undesirable plants. The following are examples of suitable crops:

*Allium cepa, Ananas comosus, Arachis hypogaea, Asparagus officinalis, Beta vulgaris* ssp. *altissima, Beta vulgaris* ssp. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* ssp., *Manihot esculenta, Medicago sativa, Musa* ssp., *Nicotiana tabacum* (*N. rustica*), *Olea europaea, Oryza sativa, Phaseolus lunatus, Phaseolus vulgaris, Picea abies, Pinus* ssp., *Pisum sativum, Prunus avium, Prunus persica, Pyrus communis, Ribes sylvestre, Ricinus communis, Saccharum officinarum, Secale cereale, Solanum tuberosum, Sorghum bicolor* (*s. vulgare*), *Theobroma cacao, Trifolium pratense, Triticum aestivum, Triticum durum, Vicia faba, Vitis vinifera* and *Zea mays.*

Moreover, the compounds I can also be used in crops which tolerate the action of herbicides as a result of breeding, including genetic engineering methods.

Furthermore, the 5-pyrazolylbenzoic acid derivatives I are also suitable for desiccating and/or defoliating plants.

As desiccants, they are particularly suitable for desiccating the aerial parts of crop plants such as potatoes, oil seed rape, sunflower and soya bean. This allows completely mechanical harvesting of these important crop plants.

Also of economic interest is to facilitate harvesting, which is made possible by concentrating, over a period of time, dehiscence, or reducing the adhesion to the tree, in citrus fruit, olives or other species and varieties of pomaceous fruit, stone fruit and nuts. The same mechanism, i.e. promotion of the formation of abscission tissue between fruit or leaf and shoot of the plants, is also important for readily controllable defoliation of useful plants, in particular cotton.

Moreover, shortening the period within which the individual cotton plants mature results in an improved fiber quality after harvesting.

The compounds I, or the compositions comprising them, can be used for example in the form of ready-to-spray aqueous solutions, powders, suspensions, also highpercentage aqueous oily or other suspensions or dispersions, emulsions, oil dispersions, pastes, dusts, materials for spreading or granules, by means of spraying, atomizing, dusting, spreading or pouring. The use forms depend on the intended aims; in any case, they should guarantee the finest possible distribution of the active ingredients according to the invention.

Suitable inert auxiliaries for the preparation of ready-to-spray solutions, emulsions, pastes or oil dispersions are mainly: mineral oil fractions of medium to high boiling point, such as kerosene and diesel oil, furthermore coal tar oils and oils of vegetable or animal origin, aliphatic, cyclic and aromatic hydrocarbons, e.g. paraffins, tetrahydronaphthalene, alkylated naphthalenes and their derivatives, alkylated benzenes and their derivatives, alcohols, such as methanol, ethanol, propanol, butanol and cyclohexanol, ketones, such as cyclohexanone, strongly polar solvents, e.g. amines, such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the substances, either as such or dissolved in an oil or solvent, can be homogenized in water by means of a wetting agent, tackifier, dispersant or emulsifier. Alternatively, it is possible to prepare concentrates comprising active ingredient, wetting agent, tackifier, dispersant or emulsifier and, if desired, solvent or oil, which are suitable for dilution with water.

Suitable surfactants (adjuvants) are the alkali metal salts, alkaline earth metal salts and ammonium salts of aromatic sulfonic acids, eg. ligno-, phenol-, naphthalene- and dibutylnaphthalenesulfonic acid, or of fatty acids, alkyl- and alkylarylsulfonates, alkyl, lauryl ether and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl polyglycol ether, tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

Powders, materials for spreading and dusts can be prepared by mixing or grinding the active ingredients together with a solid carrier.

Granules, e.g. coated granules, impregnated granules and homogeneous granules, can be prepared by binding the active ingredients to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers, such as ammonium sulfate, ammonium phosphate, ammonium nitrate, ureas, and products of vegetable origin, such as cereal meal, tree bark meal, wood meal and nutshell meal, cellulose powders, or other solid carriers.

The concentrations of the active ingredients I in the ready-to-use preparations can be varied within wide limits. In general, the formulations comprise approximately from 0.001 to 98% by weight, preferably 0.01 to 95% by weight, of at least one active ingredient. The active ingredients are employed in a purity of from 90% to 100%, preferably 95% to 100% (in accordance with NMR spectrum).

The formulation examples which follow illustrate the production of such preparations:

I. 20 parts by weight of the compound No. Ia.003 are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion comprising 0.02% by weight of the active ingredient.

II. 20 parts by weight of the compound No. Ia.004 are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion comprising 0.02% by weight of the active ingredient.

III. 20 parts by weight of the active ingredient No. Ia.006 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion comprising 0.02% by weight of the active ingredient.

IV. 20 parts by weight of the active ingredient No. Ia.007 are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture comprising 0.1% by weight of the active ingredient.

V. 3 parts by weight of the active ingredient No. Ia.008 are mixed with 97 parts by weight of finely divided kaolin. This gives a dust comprising 3% by weight of the active ingredient.

VI. 20 parts by weight of the active ingredient No. Ia.009 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the compound No. Ia.010 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of the compound No. Ia.022 is dissolved in a mixture composed of 80 parts by weight of cyclohexanone and 20 parts by weight of Wettol® EM 31 (=nonionic emulsifier based on ethoxylated castor oil). This gives a stable emulsion concentrate.

The active ingredients I, or the herbicidal compositions can be applied pre- or post-emergence. If the active ingredients are less well tolerated by certain crop plants, application techniques may be used in which the herbicidal compositions are sprayed, with the aid of the spraying equipment, in such a way that they come as little as possible into contact with the leaves of the sensitive crop plants, while the active ingredients reach the leaves of undesirable plants which grow under these crop plants, or the naked soil surface (post-directed, lay-by).

Depending on the intended aim, the season, the target plants and the growth stage, the application rates of active ingredient I are from 0.001 to 3.0, preferably 0.01 to 1.0, kg of active ingredient (a.i.) per ha.

To widen the spectrum of action, and to achieve synergistic effects, the 5-pyrazolylbenzoic acid derivatives I may be mixed with a large number of representatives of other groups of herbicidal or growth-regulating ingredients and then applied concomitantly. Suitable components for mixtures are for example 1,2,4-thiadiazoles, 1,3,4-thiadiazoles, amides, aminophosphoric acid and its derivatives, aminotriazoles, anilides, aryloxy/hetaryloxyalkanoic acids and their derivatives, benzoic acid and its derivatives, benzothiadiazinones, 2-(hetaroyl/aroyl)-1,3-cyclohexanediones, hetaryl aryl ketones, benzylisooxazolidinones, meta-CF$_3$-phenyl derivatives, carbamates, quinolinecarboxylic acid and its derivatives, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be advantageous to apply the compounds I, alone or in combination with other herbicides, together with further crop protection agents, for example with pesticides or agents for controlling phytopathogenic fungi or bacteria. Also of interest is the miscibility with mineral salt solutions, which are employed for treating nutrient and trace element deficiencies. Non-phytotoxic oils and oil concentrates may also be added.

PREPARATION EXAMPLES

Example 1

Synthesis of the precursor 5-(4-chloro-5-difluoromethoxy-1-methyl-1H-pyrazol-3-yl)-2,4-dichlorobenzoic acid:

Step 1: 5-(2,4-Dichloro-5-methylphenyl)-1,2-dihydro-2-methyl-3H-pyrazol-3-one 13.5 g (292 mmol) of methylhydrazine were slowly added to 80.4 g (292 mmol) of ethyl 2,4-dichloro-5-methylbenzoylacetate in 300 ml of diethylene glycol dimethyl ether. After 4 hours at 100° C., the solution was stirred into 1 l of ice-water. The precipitate formed was filtered off, washed with a small amount of methylene chloride and dried. Yield: 38.8 g.

$^1$H NMR (270 MHz, in $d^6$-dimethyl sulfoxide): δ [ppm]= 2.32 (s,3H), 3.60 (s,3H), 5.89 (s,1H), 7.58 (s,1H), 7.76 (s,1H), 11.12 (s,1H).

Step 2: 3-(2,4-Dichloro-5-methylphenyl)-5-difluoromethoxy-1-methyl-1H-pyrazole 28.8 g (720 mmol) of sodium hydroxide dissolved in 240 ml of water were added to a solution of 37 g (144 mmol) of 5-(2,4-dichloro-5-methylphenyl)-1,2-dihydro-2-methyl-3H-pyrazol-3-one in 390 ml of dioxane. Chlorodifluoromethane was subsequently passed in at 60–65° C. in the course of 4 hours, whereupon the reaction solution was stirred into 1 l of water. It was then extracted using methyl tert-butyl ether. The organic phase was dried over magnesium sulfate, filtered and then concentrated. The crude product was purified by means of column chromatography on silica gel (eluent: diethyl ether). Yield: 35.1 g.

$^1$H NMR (270 MHz, in CDCl$_3$): δ [ppm]=2.39 (s,3H), 3.84 (s,3H), 6.45 (s,1H), 6.59 (t,1H), 7.46 (s,1H), 7.70 (s,1H).

Step 3: 4-Chloro-3-(2,4-dichloro-5-methylphenyl)-5-difluoromethoxy-1-methyl-1H-pyrazole 16.9 g (125 mmol) of sulfuryl chloride were added dropwise to a solution of 35 g (114 mmol) of 3-(2,4-dichloro-5-methylphenyl)-5-difluoromethoxy-1-methyl-1H-pyrazole in 120 ml of tetrachloromethane. After the reaction mixture had been stirred for 2 hours, it was washed with water, saturated aqueous sodium hydrogen carbonate solution and saturated aqueous sodium chloride solution, and then dried over magnesium sulfate, filtered and concentrated. Yield: 30.8 g.

$^1$H NMR (270 MHz, in CDCl$_3$): δ [ppm]=2.39 (s,3H), 3.85 (s,3H), 6.74 (t,1H), 7.30 (s,1H), 7.49 (s,1H).

Step 4: 3-(5-Dibromomethyl-2,4-dichlorophenyl)-4-chloro-5-difluoromethoxy-1-methyl-1H-pyrazole 99.3 g (560 mmol) of N-bromosuccinimide were added to a solution of 28 g (82 mmol) of 4-chloro-3-(2,4-dichloro-5-methylphenyl)-5-difluoromethoxy-1-methyl-1H-pyrazole in 1.5 l of tetrachloromethane. The reaction mixture was then irradiated for 2 hours using a UV lamp and a 150 W high-pressure mercury vapor lamp. The solids content was subsequently filtered off, whereupon the filtrate was concentrated. Yield: quantitative.

$^1$H NMR (270 MHz, in CDCl$_3$): δ [ppm]=3.88 (s,3H), 6.75 (t,1H), 7.05 (s,1H), 7.50 (s,1H), 8.08 (s,1H).

Step 5: 5-(4-Chloro-5-difluoromethoxy-1-methyl-1H-pyrazol-3-yl)-2,4-dichlorobenzaldehyde 45.5 g (91 mmol) of 3-(5-dibromomethyl-2,4-dichlorophenyl)-4-chloro-5-difluoromethoxy-1-methyl-1H-pyrazole were added, a little at a time, to 65 ml of concentrated sulfuric acid at 85° C., during which process the mixture was heated slowly to 95° C. The reaction mixture was subsequently stirred at 103° C. for a further 5 minutes, whereupon it was stirred into 600 ml of ice-water. The product was extracted using dichloromethane. The organic phase was washed using saturated sodium chloride solution, dried over magnesium sulfate, filtered and finally concentrated. The crude product was purified by dissolving in hexane/ethyl acetate (1:1) and filtering the solution through a silica gel bed. Yield after concentration: 20 g.

$^1$H NMR (270 MHz, in CDCl$_3$): δ [ppm]=3.87 (s,3H), 6.77 (t,1H), 7.65 (s,1H), 8.02 (s,1H), 10.41 (s,1H).

Step 6: 5-(4-Chloro-5-difluoromethoxy-1-methyl-1H-pyrazol-3-yl)-2,4-dichlorobenzoic acid A solution of 2.5 g (16 mmol) of sodium dihydrogen phosphate dihydrate in 25 ml of water was added dropwise at 10–15° C. to a solution of 21.3 g (60 mmol) of 5-(4-chloro-5-difluoromethoxy-1-methyl-1H-pyrazol-3-yl)-2,4-dichlorobenzaldehyde in 120 ml of acetonitrile. 6 ml of a 30% by weight hydrogen peroxide solution and then, in the course of two hours, a solution of 8.7 g (96 mmol) of sodium chlorite in 80 ml of water were added dropwise to this mixture. The reaction mixture was stirred for a further hour and then acidified with 3 N hydrochloric acid. The solids content was separated from the resulting suspension and dried. Yield: 13.7 g; m.p. 159–160° C.

Example 2

2-(Ethoxyimino)ethyl 5-(4-chloro-5-difluoromethoxy-1-methyl-1H-pyrazol-3-yl)-2,4-dichlorobenzoate (No. Ia.003)

A solution of 1.9 g (5 mmol) of 5-(4-chloro-5-difluoromethoxy-1-methyl-1H-pyrazol-3-yl)-2,4-dichlorobenzoic acid, 0.9 g (6.5 mmol) of potassium carbonate (ground) and 0.6 g (5 mmol) of O-ethyl-chloroacetaldehyde oxime in 50 ml of dimethylformamide was stirred for 3 hours at 50–60° C., whereupon it was concentrated. The residue was taken up in ethyl acetate and water. The aqueous phase was subsequently separated off and again mixed briefly with ethyl acetate. The combined organic phases were dried over magnesium sulfate and then filtered and concentrated. The crude product was purified by means of column chromatography on silica gel (eluent: hexane/ethyl acetate =4:1). Yield: 1.6 g.

$^1$H NMR (250 MHz, in CDCl$_3$): δ [ppm]=1.26 (m,3H), 3.85 (s,3H), 4.10–4.23 (m,2H), 4.90 and 5.12 (2d, together 2H), 6.71 (t,1H), 6.88 and 7.54 (2t, together 1H), 7.62 (m,1H), 8.02 (m,1H).

Example 3

2-(2-Pyrrolidon-1-yl)ethyl 5-(4-Chloro-5-difluoromethoxy-1-methyl-1H-pyrazol-3-yl)-2,4-dichlorobenzoate (No. Ia.331)

A solution of 1 g (2.6 mmol) of 5-(4-chloro-5-difluoromethoxy-1-methyl-1H-pyrazol-3-yl)-2,4-dichlorobenzoyl chloride and 0.5 g (3.8 mmol) of 2-(2-pyrrolidon-1-yl)ethanol in 20 ml of pyridine was stirred for approximately 15 hours, whereupon the reaction mixture was concentrated. The residue was treated with 10 ml of water and 20 ml of ethyl acetate. The organic phase was then separated off, dried over magnesium sulfate and concentrated. The crude product was purified by column chromatography on silica gel (eluent: initially hexane/ethyl acetate= 1:1, then ethyl acetate). Yield: 0.8 g.

Precursor:

5-(4-Chloro-5-difluoromethoxy-1-methyl-1H-pyrazol-3-yl)-2,4-dichlorobenzoyl chloride 20.5 g (160 mmol) of oxalyl chloride were added dropwise to a solution of 7.7 g (20 mmol) of 5-(4-chloro-5-difluoromethoxy-1-methyl-1H-pyrazol-3-yl)-2,4-dichlorobenzoic acid in 300 ml of toluene. After 6 hours stirring at reflux temperature, the reaction mixture was concentrated. Yield: quantitative.

$^1$H NMR (250 MHz, in CDCl$_3$): δ [ppm]=3.87 (s,3H), 6.72 (t,1H), 7.66 (s,1H), 8.21 (s,1H).

Example 4

2-(Allyloxyimino)ethyl 5-(4-Chloro-5-difluoromethoxy-1-methyl-1H-pyrazol-3-yl)-2,4-dichlorobenzoate (No. Ia.005)

A solution of 2 g (5 mmol) of 5-(4-chloro-5-difluoromethoxy-1-methyl-1H-pyrazol-3-yl)-2,4-dichlorobenzoyl chloride and 0.6 g (5 mmol) of O-allyl glycolaldehyde oxime in 40 ml of pyridine was heated for 5 hours at 50–60° C., whereupon the mixture was concentrated. The residue was taken up in ethyl acetate. The solution obtained was washed using 2 N hydrochloric acid and saturated sodium chloride solution, dried over magnesium sulfate, filtered and then concentrated. The crude product was purified by column chromatography on silica gel (eluent: hexane/ethyl acetate 1:1). Yield: 1.2 g.

$^1$H NMR (250 MHz, in CDCl$_3$): δ [ppm]=3.84 (s,3H), 4.55–4.66 (m,2H), 4.91 and 5.12 (2d, together 2H), 5.20–5.37 (m,2H), 5.88–6.08 (m,1H), 6.71 (t,1H), 6.92 and 7.60 (2t, together 1H), 7.64 (m,1H), 8.00 (m,1H).

Example 5

N-[2-(1,3-dioxolan-2-yl)ethyl]-N-methyl-5-(4-chloro-5-difluoromethoxy-1-methyl-1H-pyrazol-3-yl)-2,4-dichlorobenzamide (No. Ia.458)

After a solution of 1 g (2.7 mmol) of 5-(4-chloro-5-difluoromethoxy-1-methyl-1H-pyrazol-3-yl)-2,4-dichlorobenzoic acid and 0.66 g (4.1 mmol) of 1,1-carbonyldiimidazole had been stirred for 1 hour in 20 ml of tetrahydrofuran, 0.55 g (4.1 mmol) of N-[2-(1,3-dioxolan-2-yl)-ethyl]-N-methylamine were added. The mixture was subsequently stirred for a further 16 hours at approximately 20° C. The reaction mixture was then concentrated. The crude product was purified by chromatography on silica gel (eluent: hexane/ethyl acetate=1:1). Yield: 0.4 g.

In addition to the compounds described above, Tables 2 and 3 below show more 5-pyrazolylbenzoic acid derivatives I, which were prepared, or can be prepared, in a similar manner:

TABLE 2

Ia

{$R^1$ = CH$_3$;
$R^2$ = OCHF$_2$;
$R^3$, $R^4$, $R^5$ = Cl}

| No. | $R^6$ | M.p./$^1$H NMR [ppm] /MS [m/z] |
|---|---|---|
| Ia.002 | —O—CH$_2$—CH=N—O—CH$_3$ | 3.85(s, 3H), 3.90 and 3.94(25, together 3H), 4.90 and 5.10(2d, together 2H), 6.73(t, 1H), 6.90 and 7.35(2t, together 1H), 7.63(m, 1H), 7.99(m, 1H) |
| Ia.003 | —O—CH$_2$—CH=N—O—C$_2$H$_5$ | 1.26(m, 3H), 3.85(s, 3H), 4.10–4.23(m, 2H), 4.90 and 5.12(2d, together 2H), 6.71(t, 1H), 6.88 and 7.54(2t, together 1H), 7.62(m, 1H), 8.02(m, 1H) |
| Ia.004 | —O—CH$_2$—CH=N—O—CH$_2$—CH$_2$—C$_2$H$_5$ | 0.94(m, 3H), 1.40(m, 2H), 1.65(m, 2H), 3.86 (s, 3H), 4.08–4.17(m, 2H), 4.90 and 5.11(2d, together 2H), 6.71(t, 1H), 6.87 and 7.55(2t, together 1H), 7.64(m, 1H), 8.00(m, 1H) |
| Ia.005 | —O—CH$_2$—CH=N—O—CH$_2$—CH=CH$_2$ | 3.84(s, 3H), 4.55–4.66(m, 2H), 4.91 and 5.12 (2d, together 2H), 5.20–5.37(m, 2H), 5.88–6.08 (m, 1H), 6.71(t, 1H), 6.92 and 7.60(2t, together 1H), 7.64(m, 1H), 8.00(m, 1H) |
| Ia.006 | —O—CH$_2$—CH=N—O—CH$_2$—CH=CHCl | 3.87(s, 3H), 4.54–4.64(m, 2H), 4.91 and 5.11 (2d, together 2H), 6.04–6.17(m, 1H), 6.30 (d, 1H), 6.73(t, 1H), 6.93 and 7.48(2t, together 1H), 7.65(m, 1H), 8.01(m, IH) |
| Ia.007 | —O—CH$_2$—CH=N—O—CH$_2$—CH=CH—CH$_3$ | 1.74(d, 3H), 3.86(s, 3H), 4.50–4.73(m, 2H), 4.90 and 5.12(2d, together 2H), 5.57–5.86(m, 2H), 6.71(t, 1H), 6.90 and 7.57(2t, together 1H), 7.64 (m, 1H), 8.00(m, 1H) |

TABLE 2-continued

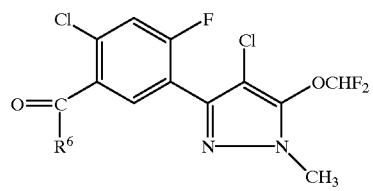

{R¹ = CH₃;
R² = OCHF₂;
R³, R⁴, R⁵ = Cl}

| No. | R⁶ | M.p./¹H NMR [ppm] /MS [m/z] |
|---|---|---|
| Ia.008 | —O—CH₂—CH=N—O—CH₂-phenyl | 3.86(s, 3H), 4.50–4.73(m, 2H), 4.91 and 5.16 (2d, together 2H), 5.14(m, 2H) 6.71(t, 1H), 6.93 and 7.62(2t, together 1H), 7.35(m, 5H), 7.64 (m, 1H), 7.99(m, 1H) |
| Ia.009 | —O—CH₂—CH=N—O—CH₂-(4-chlorophenyl) | 3.86(s, 3H), 4.90 and 5.13(2d, together 2H), 5.08 and 5.11(2s, together 2H) 6.71(t, 1H), 6.93 and 7.61(2t, together 1H), 7.31(m, 4H), 7.64 (m, 1H), 7.99(m, 1H) |
| Ia.010 | —O—CH₂—CH=N—O—CH₂-(2-chlorothiophen-5-yl) | 558 [M+H]⁺ |
| Ia.019 | —O—CH₂—C(CH₃)=N—O—C₂H₅ | 1.28(t, 3H), 1.95(s, 3H), 3.85(s, 3H), 4.14 (q, 2H), 4.86 and 5.15(2S, together 2H), 6.71 (t, 1H), 7.62(s, 1H), 7.98(s, 1H) |
| Ia.021 | —O—CH₂—C(CH₃)=N—O—CH₂—CH=CH₂ | 55–58° C. |
| Ia.022 | —O—CH₂—C(CH₃)=N—O—CH₂—CH=CHCl | 98–100° C. |
| Ia.228 | —O—CH₂—CH₂—O—N=C(CH₃)2 | 1.85(s, 6H), 3.85(s, 3H), 4.34(m, 2H), 4.55 (m, 2H) 6.73(t, 1H), 7.62(s, 1H), 7.99(s, 1H) |
| Ia.270 | —O—CH₂—CH₂—SO₂—CH₃ | 98–100° C. |
| Ia.274 | —O—CH₂—CH₂—SO₂-phenyl | 136–137° C. |
| Ia.311 | —O—(3-acetoxy-tetrahydrofuran-4-yl) | 2.07(s, 3H), 3.86(s, 3H), 3.95–4.13(m, 4H), 5.40-5.62(m, 2H) 6.72(t, 1H), 7.64(m, 1H), 7.95 (m, 1H) |
| Ia.331 | O—CH₂—CH₂—(2-pyrrolidon-1-yl) | 127–128° C. |
| Ia.440 | —NH—(sulfolan-3-yl) | 487 [M⁺], 353 |
| Ia.443 | NH—(dihydro-(3H)-tbiopben-2-on-3-yl) | 135–137° C. |
| Ia.458 | N(CH₃)—CH₂—CH₂—(1,3-dioxolan-2-yl) | 97–98° C. |

TABLE 3

{R¹ = CH₃;
R² = OCHF₂;
R³, R⁵ = Cl; R⁴ = F}

| No. | R⁶ | M.p./¹H-NMR [ppm]/MS[m/z] |
|---|---|---|
| Ib.002 | —O—CH₂—CH=N—O—CH₃ | 3.85(s, 3H), 3.90 and 3.95(2S, together 3H), 4.92 and 5.12(2d, together 2H), 6.73(t, 1H), 6.89 and 7.55(2t, together 1H), 7.34(m, 1H), |
| Ib.003 | —O—CH₂—CH=N—O—C₂H₅ | 1.30(m, 3H), 3.86(s, 3H), 4.10–4.20(m, 2H), 4.92 and 5.12(2d, together 2H), 6.72(t, 1H), 6.89 and 7.55(2t, together 1H), 7.34(m, 1H), |
| Ib.004 | —O—CH₂—CH=N—O—CH₂—CH₂—C₂H₅ | 0.92(m, 3H), 1.40(m, 2H), 1.65(m, 2H), 3.85 (s, 3H), 4.12(m, 2H), 4.91 and 5.12(2d, together 2H), 6.71(t, 1H), 6.88 and 7.55(2t, together 1H), 7.32(m, 1H), 8.18(m, 1H) |
| Ib.005 | —O—CH₂—CH=N—O—CH₂—CH=CH₂ | 3.85(s, 3H), 4.60 and 4.63(2d, together 2H), 4.91 and 5.13(2d, together 2H), 5.20–5.35 (m, 2H), 5.90–6.05(m, 1H), 6.70(t, 1H), 6.91 and 7.60(2t, together 1H), 7.34(m, 1H), 8.16(m, 1H) |

TABLE 3-continued

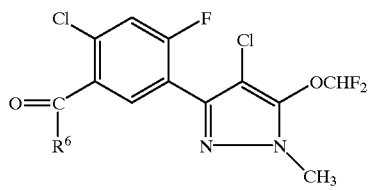

Ib

{R¹ = CH₃;
R² = OCHF₂;
R³, R⁵ = Cl; R⁴ = F}

| No. | R⁶ | M.p./¹H-NMR [ppm]/MS[m/z] |
|---|---|---|
| Ib.006 | —O—CH₂—CH=N—O—CH₂—CH=CHCl | 3.86(s, 3H), 4.57 and 4.62(2d, together 2H), 4.91 and 5.11(2d, together 2H), 6.04–6.17 (m, 1H), 6.25–6.34(m, 1H), 6.71(t, 1H), 6.93 and 7.58(2t, together 1H), 7.34(m, 1H), 8.17(m, 1H) |
| Ib.007 | O—CH₂—CH=N—O—CH₂—CH=CH—CH₃ | 1.75(d, 3H), 3.86(s, 3H), 4.50–4.74(m, 2H), 4.91 and 5.13(2d, together 2H), 5.60–5.85(m, 2H), 6.71(t, 1H), 6.91 and 7.57(2t, together 1H), 7.33 (m, 1H), 8.16(m, 1H) |
| Ib.019 | —O—CH₂—C(CH₃)=N—O—C₂H₅ | 74–76° C. |
| Ib.021 | —O—CH₂—C(CH₃)=N—O—CH₂—CH=CH₂ | 61–63° C. |
| Ib.022 | —O—CH₂—C(CH₃)=N—O—CH₂—CH=CHCl | 81–84° C. |
| Ib.100 | —NH—CH₂—CH=N—O—CH₃ | 3.85(s, 3H), 3.87 and 3.94(2d, together 3H), 4.204.40(m, 2H), 6.70 and 6.80(25, together 1H), 6.72(t, 1H), 6.85 and 7.51(2t, together 1H), 7.30(d, 1H), 7.95(m, 1H) |
| Ib.228 | —O—CH₂—CH₂—O—N=C(CH₃)2 | 33–36° C. |
| Ib.270 | —O—CH₂—CH₂—SO₂—CH₃ | 3.03(s, 3H), 3.49(t, 2H), 3.85(s, 3H), 4.81 (t, 2H), 6.72(t, 1H), 7.34(d, 1H), 8.16(d, 1H) |
| Ib.274 | —O—CH₂—CH₂—SO₂-phenyl | 82–88° C. |
| Ib.297 | —O—CH₂-(oxiran-2-yl) | 410 [M]⁺, 337 |
| Ib.365 | —O—CH₂-(tetrahydro-4H-pyran-4-yl) | 452 [M9 ⁺ |
| Ib.478 | —O—CH₂-(1,3-dioxolan-2-yl) | 440 [M]⁺, 337 |

USE EXAMPLES (HERBICIDAL ACTIVITY)

The herbicidal action of the 5-pyrazolylbenzoic acid derivatives I was demonstrated by the following greenhouse experiments:

The culture containers used were plastic flowerpots containing loamy soil with approximately 3.0% of humus as the substrate. The seeds of the test plants were sown in species by species.

In the case of pre-emergence treatment, the active ingredients which were suspended or emulsified in water were applied directly after sowing by means of finely distributing nozzles. The containers were irrigated gently to promote germination and growth and then covered with transparent plastic hoods until the plants had rooted. This cover causes uniform germination of the test plants, unless this was adversely affected by the active ingredients.

For the purposes of post-emergence treatment, the test plants were first grown to a plant height of 3 to 15 cm, depending on the growth form, and only then treated with the active ingredients which were suspended or emulsified in water. To this end, the test plants were either sown directly and grown on in the same containers, or they were first grown separately as seedlings and transplanted into the test containers a few days prior to treatment. The rate of application for the post-emergence treatment was 0.0156 or 0.0078 kg of a.i. (active ingredient) per ha.

Depending on the species, the plants were kept at from 10 to 25° C. or 20 to 35° C. The test period extended over 2 to 4 weeks. During this time, the plants were tended, and their response to individual treatments was evaluated.

A scale from 0 to 100 was used for the assessment. 100 means no emergence of the plants or complete destruction of at least the aerial parts, and 0 means no damage or normal growth.

The plants used in the greenhouse experiments were composed of the following species:

| Scientific name | Common name |
|---|---|
| Amaranthus retroflexus | Redroot pigweed |
| Galium aparine | Catchweed bedstraw |
| Polygonum persicaria | Lady's thumb |
| Solanum nigrum | Black nightshade |
| Veronica subspecies | Speedwell |

At application rates of 0.0156 and 0.0078 kg of a.i. per ha, the compound No. Ia.003 had a very good action against the abovementioned plants when applied post-emergence.

USE EXAMPLES (DESICCANT/DEFOLIANT ACTIVITY)

The test plants used were young cotton plants with 4 leaves (without cotyledons) which were grown under greenhouse conditions (relative atmospheric humidity 50 to 70%; day/night temperature=27/20° C).

The young cotton plants underwent foliar treatment to drip point with aqueous preparations of the active ingredients (with an addition of 0.15% by weight, based on the spray mixture, of the fatty alcohol alkoxylate Plurafac LF® 700, which acts as a surfactant). The amount of water applied was 1000 l/ha (converted). After 13 days, the number of shed leaves and the degree of defoliation in % were determined.

No leaves were shed in the untreated control plants.

We claim:
1. A 5-pyrazolylbenzoic acid compound of the formula I

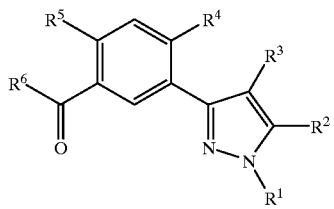

where the substituents have the following meanings:
$R^1$ is hydrogen, $C_1$–$C_4$-alkyl, cyano-$C_1$–$C_4$-alkyl or $C_1$–$C_4$-haloalkyl;
$R^2$ is $C_1$–$C_4$-alkoxy, $C_1$–$C_4$-alkylthio, $C_1$–$C_4$-haloalkoxy or $C_1$–$C_4$-haloalkylthio;
$R^3$ is hydrogen, cyano, nitro or halogen;
$R^4$ is halogen;
$R^5$ is cyano, halogen, $C_1$–$C_4$-alkyl, $C_1$–$C_4$-haloalkyl, $C_1$–$C_4$-alkoxy or $C_1$–$C_4$-haloalkoxy;
$R^6$ is —O—$R^7$, —S—$R^7$, —N($R^8$)—$R^7$ or —N($R^8$)—O$R^7$;
$R^7$ is —X—C($R^9$)=N—O—$R^{10}$, —X—C($R^9$)=N—O—Z—$R^{10}$, —X—O—N=C($R^{11}$,$R^{12}$) or —X—SO$_2$—$R^{13}$;
$R^8$ is hydrogen, $C_1$–$C_4$-alkyl, $C_1$–$C_4$-haloalkyl, $C_3$–$C_5$-alkenyl, $C_3$–$C_5$-haloalkenyl, $C_3$–$C_5$-alkynyl or $C_1$–$C_4$-alkylsulfonyl;
$R^9$ is hydrogen, cyano, $C_1$–$C_4$-alkyl, $C_1$–$C_4$-alkoxy or $C_1$–$C_4$-alkylthio;
$R^{10}$ is hydrogen, $C_1$–$C_4$-alkyl, $C_1$–$C_4$-haloalkyl, $C_1$–$C_4$-cyanoalkyl, di($C_1$–$C_4$-alkyl)amino-$C_1$–$C_4$-alkyl, $C_1$–$C_4$-alkoxy-$C_1$–$C_4$-alkyl, $C_1$–$C_4$-alkylthio-$C_1$–$C_4$-alkyl, ($C_1$–$C_4$-alkyl)carbonyl, ($C_1$–$C_4$-alkoxy)carbonyl, di($C_1$–$C_4$-alkyl)aminocarbonyl, ($C_1$–$C_4$-haloalkyl)carbonyl, $C_3$–$C_5$-alkenyl, $C_3$–$C_5$-haloalkenyl, di($C_1$–$C_4$-alkyl)amino-$C_3$–$C_5$-alkenyl, $C_1$–$C_4$-alkoxy-$C_3$–$C_5$-alkenyl, $C_1$–$C_4$-alkylthio-$C_3$–$C_5$-alkenyl, $C_3$–$C_5$-alkynyl, $C_3$–$C_5$-haloalkynyl, $C_3$–$C_7$-cycloalkyl which is unsubstituted or carries one to three $C_1$–$C_3$-alkyl radicals, or is phenyl, benzoyl or 5- or 6-membered heteroaryl which contains one to three hetero atoms selected from the group consisting of three nitrogen atoms and one oxygen and sulfur atom, it being possible for the phenyl and heteroaryl rings to be unsubstituted or to have attached to each substitutable ring member one of the following substituents: nitro, cyano, halogen, $C_1$–$C_4$-alkyl, $C_1$–$C_4$-haloalkyl or $C_1$–$C_4$-alkoxy;
$R^{11}$, $R^{12}$ independently of one another are hydrogen, $C_1$–$C_4$-alkyl, $C_1$–$C_4$-haloalkyl, $C_1$–$C_4$-alkoxy-$C_1$–$C_4$-alkyl, $C_3$–$C_5$-alkenyl, $C_3$–$C_5$-haloalkenyl, $C_3$–$C_5$-alkynyl, $C_3$–$C_5$-haloalkynyl, $C_3$–$C_7$-cycloalkyl, which is unsubstituted or carries one to three $C_1$–$C_3$-alkyl radicals, or are phenyl which is unsubstituted or carries up to five substituents selected from the group consisting of: nitro, cyano, halogen, $C_1$–$C_4$-alkyl, $C_1$–$C_4$-haloalkyl and $C_1$–$C_4$-alkoxy, or
$R^{11}$ and $R^{12}$ together with the joint carbon atom to which they are bonded form a saturated 3- to 8-membered ring consisting of methylene ring members, or methylene ring members and one or two oxygen, sulfur and/or aza ring members, it being possible for the ring to be unsubstituted or to have attached to it one to four $C_1$–$C_4$-alkyl radicals;
$R^{13}$ is $C_1$–$C_4$-alkyl, $C_1$–$C_4$-haloalkyl, $C_1$–$C_4$-cyanoalkyl, di($C_1$–$C_4$-alkyl)amino-($C_1$–$C_4$-alkyl), $C_1$–$C_4$-alkoxy-$C_1$–$C_4$-alkyl, $C_1$–$C_4$-alkylthio-$C_1$–$C_4$-alkyl, $C_3$–$C_5$-alkenyl, $C_3$–$C_5$-haloalkenyl, di($C_1$–$C_4$-alkyl)amino-$C_3$–$C_5$-alkenyl, $C_1$–$C_4$-alkoxy-$C_3$–$C_5$-alkenyl, $C_1$–$C_4$-alkylthio-$C_3$–$C_5$-alkenyl, $C_3$–$C_5$-alkynyl, $C_3$–$C_5$-haloalkynyl, $C_3$–$C_7$-cycloalkyl which is unsubstituted or carries one to three $C_1$–$C_3$-alkyl radicals, or is phenyl, or is 5- or 6-membered heteroaryl which contains one to three hetero atoms selected from the group consisting of three nitrogen atoms and one oxygen or sulfur atom, it being possible for the phenyl and heteroaryl ring to be unsubstituted or to have attached to each substitutable ring member one of the following substituents: nitro, cyano, halogen, $C_1$–$C_4$-alkyl, $C_1$–$C_4$-haloalkyl or $C_1$–$C_4$-alkoxy;
X and Z independently of one another are $C_1$–$C_4$-alkylene chains which are unsubstituted or carry one to four substituents selected from the group consisting of halogen, $C_1$–$C_4$-alkyl, $C_1$–$C_4$-haloalkyl and $C_1$–$C_4$-alkoxy;
or an agriculturally useful salt of a compound I.

2. The 5-pyrazolylbenzoic acid compound of the formula I defined in claim 1 wherein $R^1$ is $C_1$–$C_4$-alkyl.

3. The 5-pyrazolylbenzoic acid compound of the formula I defined in claim 1 wherein $R^2$ is $C_1$–$C_4$-haloalkoxy.

4. The 5-pyrazolylbenzoic acid compound of the formula I defined in claim 1 wherein $R^3$ is halogen.

5. The 5-pyrazolylbenzoic acid compound of the formula I defined in claim 1 wherein $R^5$ is halogen or $C_1$–$C_4$-haloalkyl.

6. The 5-pyrazolylbenzoic acid compound of the formula I defined in claim 1 wherein $R^6$ is $OR^7$ or $N(R^8)R^7$.

7. The 5-pyrazolylbenzoic acid compound of the formula I defined in claim 1 wherein $R^7$ is —X—C($R^9$)=N—O—$R^{10}$, —X—C($R^9$)=N—O—Z—$R^{10}$ or —X—O—N=C($R^{11}$,$R^{12}$).

8. The 5-pyrazolylbenzoic acid compound of the formula I defined in claim 1 wherein $R^7$ is —X—C($R^9$)=N—O—Z—$R^{10}$ or —X—O—N=C($R^{11}$,$R^{12}$).

9. The 5-pyrazolylbenzoic acid compound of the formula I defined in claim 1 wherein $R^8$ or $R^9$ is hydrogen or $C_1$–$C_4$-alkyl.

10. The 5-pyrazolylbenzoic acid compound of the formula I defined in claim 1 wherein $R^{10}$ is hydrogen, $C_1$–$C_4$-alkyl, $C_1$–$C_4$-haloalkyl, $C_1$–$C_4$-alkoxy-$C_1$–$C_4$-alkyl, $C_3$–$C_5$-alkenyl, $C_3$–$C_5$-haloalkenyl, $C_3$–$C_5$-alkynyl, $C_3$–$C_5$-haloalkynyl, $C_3$–$C_7$-cycloalkyl which is unsubstituted or carries one to three $C_1$–$C_3$-alkyl radicals, or is phenyl, benzoyl or 5- or 6-membered heteroaryl which contains one to three hetero atoms selected from the group consisting of three nitrogen atoms and one oxygen or sulfur atom, it being possible for the phenyl and heteroaryl rings to be unsubstituted or to have attached to each substitutable ring member one of the following substituents: nitro, cyano, halogen, $C_1$–$C_4$-alkyl, $C_1$–$C_4$-haloalkyl or $C_1$–$C_4$-alkoxy.

11. The 5-pyrazolylbenzoic acid compound of the formula I defined in claim 1 wherein $R^{11}$ or $R^{12}$ is hydrogen, $C_1$–$C_4$-alkyl, $C_1$–$C_4$-haloalkyl, $C_3$–$C_5$-alkenyl, $C_3$–$C_5$-alkynyl, $C_3$–$C_7$-cycloalkyl or phenyl which is unsubstituted or carries one to five substituents selected from the groups consisting of: nitro, cyano, halogen and $C_1$–$C_4$-alkyl, or $R^{11}$ and $R^{12}$ together with the joint carbon atom to which they are bonded form a saturated 5- or 6-membered carbocyclic ring.

12. The 5-pyrazolylbenzoic acid compound of the formula I defined in claim 1 wherein $R^{13}$ is $C_1$–$C_4$-alkyl, $C_1$–$C_4$-haloalkyl, $C_1$–$C_4$-alkoxy-$C_1$–$C_4$-alkyl, $C_3$–$C_5$-alkenyl, $C_3$–$C_5$-haloalkenyl, $C_3$–$C_5$-alkynyl, phenyl, or is 5- or 6-membered heteroaryl which contains one to three hetero atoms selected from the group consisting of three nitrogen atoms and one oxygen or sulfur atom, where the phenyl and heteroaryl ring are unsubstituted or have attached to each substitutable ring member one of the following substituents: halogen or $C_1$–$C_4$-alkyl.

13. The 5-pyrazolylbenzoic acid compound of the formula I defined in claim 1 wherein X or Z is a $C_1$–$C_4$-alkylene chain which is unsubstituted or carries one to four substituents selected from the group consisting of halogen and $C_1$–$C_4$-alkyl.

14. A herbicidal composition comprising a herbicidally active amount of at least one 5-pyrazolylbenzoic acid compound of the formula I or at least one agriculturally useful salt of I as defined in claim 1, and at least one inert liquid or solid carrier and, if desired, at least one surfactant.

15. A composition for desiccating or defoliating plants comprising such an amount of at least one 5-pyrazolylbenzoic acid compound of the formula I or at least one agriculturally useful salt of I as defined in claim 1 that it acts as a desiccant or defoliant, and at least one inert liquid or solid carrier and, if desired, at least one surfactant.

16. A method of controlling undesirable vegetation, which comprises allowing a herbicidally active amount of at least one 5-pyrazolylbenzoic acid compound of the formula I or at least one agriculturally useful salt of I as defined in claim 1 to act on plants, their environment or seed.

17. A method of desiccating or defoliating plants, which comprises allowing such an amount of at least one 5-pyrazolylbenzoic acid compound of the formula I or at least one agriculturally useful salt of I as defined in claim 1 that it acts as a desiccant or defoliant to act on plants.

18. A process for the preparation of herbicidally active compositions, which comprises mixing a herbicidally active amount of at least one 5-pyrazolylbenzoic acid compound of the formula I or at least one agriculturally useful salt of I as defined in claim 1, and at least one inert liquid or solid carrier and, if desired, at least one surfactant.

19. A process for the preparation of compositions which act as desiccants or defoliants, which comprises mixing such an amount of at least one 5-pyrazolylbenzoic acid compound of the formula I or at least one agriculturally useful salt of I as defined in claim 1 that it acts as a desiccant or defoliant, and at least one inert liquid or solid carrier and, if desired, at least one surfactant.

* * * * *